US010359396B2

(12) United States Patent
Bulloch et al.

(10) Patent No.: US 10,359,396 B2
(45) Date of Patent: Jul. 23, 2019

(54) PREPARATION OF ELECTROPHORESIS GELS, AND RELATED DEVICES, SYSTEMS, AND METHODS

(71) Applicant: LIFE TECHNOLOGIES CORPORATION, Carlsbad, CA (US)

(72) Inventors: Kyle Bulloch, San Diego, CA (US); Thomas Diller, San Diego, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 123 days.

(21) Appl. No.: 15/349,106

(22) Filed: Nov. 11, 2016

(65) Prior Publication Data

US 2017/0153204 A1    Jun. 1, 2017

Related U.S. Application Data

(60) Provisional application No. 62/255,050, filed on Nov. 13, 2015.

(51) Int. Cl.
*G01N 27/447*    (2006.01)
(52) U.S. Cl.
CPC . *G01N 27/44747* (2013.01); *G01N 27/44704* (2013.01); *G01N 27/44782* (2013.01)
(58) Field of Classification Search
CPC ....... G01N 27/44747; G01N 27/44704; G01N 27/44782; G01N 27/447–453
See application file for complete search history.

(56) References Cited

U.S. PATENT DOCUMENTS

| | | | |
|---|---|---|---|
| 3,888,759 A | 6/1975 | Elson | |
| 4,294,684 A | 10/1981 | Serwer | |
| | (Continued) | | |

FOREIGN PATENT DOCUMENTS

| | | | | |
|---|---|---|---|---|
| WO | WO-9524640 A1 * | 9/1995 | .......... | B01F 15/0205 |
| WO | WO-9954721 A1 * | 10/1999 | ....... | G01N 27/44743 |
| WO | WO-2007032951 A2 * | 3/2007 | ....... | G01N 27/44704 |

OTHER PUBLICATIONS

D.R. Caprette, "Preparing SDS Gels", URL: https://web.archive.org/web/20051030035520/http://www.ruf.rice.edu/~bioslabs/studies/sds-page/gelllab2a.html, 5 pages, published Oct. 30, 2005.*

*Primary Examiner* — J. Christopher Ball

(57) ABSTRACT

An apparatus for preparation of an electrophoresis slab gel may include a base having an opening configured to receive a cassette configured to contain an electrophoresis slab gel, a clamping mechanism configured to move relative to the base between an open position in which the clamping mechanism permits insertion of a cassette into the base, and a closed position in which the clamping mechanism is configured to clamp a cassette received in the base, a compressible pad operatively coupled to the clamping mechanism in a position to compress against a cassette received in the base in the closed position of the clamping mechanism. The cassette may include a first plate and a second plate, and a spacer mechanism separate from each of the first and second plates, the spacer mechanism configured to be positioned between the inner faces of the first plate and the second plate. When subjected to a clamping force exerted on the outer faces of the first and second plates, the spacer mechanism is configured to maintain a separation distance between the inner faces of the first and second plates, and provide a seal to prevent leakage of an electrophoresis gel solution introduced between the plates.

19 Claims, 20 Drawing Sheets

(56) References Cited

U.S. PATENT DOCUMENTS

| | | | |
|---|---|---|---|
| D269,123 S | 5/1983 | Hoefer | |
| 4,560,459 A | 12/1985 | Hoefer | |
| 4,574,040 A | 3/1986 | Delony et al. | |
| 4,693,804 A | 9/1987 | Serwer | |
| 4,715,942 A | 12/1987 | Tezuka | |
| 4,772,373 A | 9/1988 | Ebata et al. | |
| 4,773,984 A | 9/1988 | Flesher et al. | |
| 4,795,541 A | 1/1989 | Hurd | |
| D303,007 S | 8/1989 | Flesher et al. | |
| 4,957,613 A | 9/1990 | Schuette | |
| 4,975,174 A | 12/1990 | Bambeck | |
| 5,073,246 A | 12/1991 | Chu | |
| 5,116,483 A | 5/1992 | Lander | |
| 5,192,408 A | 3/1993 | Scott | |
| 5,228,971 A | 7/1993 | Brumley et al. | |
| 5,238,651 A | 8/1993 | Chuba | |
| 5,284,565 A | 2/1994 | Chu | |
| 5,292,420 A | 3/1994 | Nakanura et al. | |
| 5,407,552 A | 4/1995 | Lebacq | |
| D367,713 S | 3/1996 | La Motte | |
| 5,618,399 A | 4/1997 | Gautsch | |
| 5,626,735 A | 5/1997 | Chu | |
| 5,632,877 A | 5/1997 | Van Atta et al. | |
| 5,685,967 A | 11/1997 | Manis | |
| 5,753,095 A | 5/1998 | Alpenfels | |
| 5,773,645 A | 6/1998 | Hochstrasser | |
| 5,827,418 A | 10/1998 | Haven | |
| 5,843,295 A | 12/1998 | Steiner | |
| 5,882,495 A * | 3/1999 | Garrels | G01N 27/44704 204/456 |
| 5,885,431 A * | 3/1999 | Renfrew | G01N 27/44704 204/465 |
| 5,888,369 A | 3/1999 | Tippins | |
| 5,972,188 A | 10/1999 | Rice | |
| 5,989,403 A | 11/1999 | Provonchee | |
| 6,001,233 A | 12/1999 | Levy et al. | |
| 6,027,628 A | 2/2000 | Yamamura | |
| 6,110,340 A | 8/2000 | Lau et al. | |
| 6,110,344 A | 8/2000 | Renfrew | |
| 6,139,709 A | 10/2000 | Scott | |
| D443,068 S | 5/2001 | Manusu | |
| 6,231,741 B1 * | 5/2001 | Tuurenhout | G01N 27/44704 204/618 |
| 6,379,519 B1 | 4/2002 | Sevigny | |
| 6,436,262 B1 | 8/2002 | Perez et al. | |
| 6,521,111 B1 | 2/2003 | Amshey | |
| D505,729 S | 5/2005 | Lee | |
| 6,929,732 B2 | 8/2005 | Chen | |
| 6,932,895 B2 | 8/2005 | Anderson | |
| 6,936,150 B2 | 8/2005 | Rooney et al. | |
| 6,942,775 B1 | 9/2005 | Fox et al. | |
| D510,770 S | 10/2005 | Emerson | |
| D511,386 S | 11/2005 | Emerson | |
| 6,969,455 B1 | 11/2005 | Helfer et al. | |
| D524,449 S | 7/2006 | Emerson | |
| 7,135,101 B2 | 11/2006 | Atchison et al. | |
| 7,276,143 B2 | 10/2007 | Chen et al. | |
| 7,601,251 B2 | 10/2009 | Rooney | |
| 7,749,367 B2 | 7/2010 | Zhou et al. | |
| D654,597 S | 2/2012 | Hiramura | |
| 8,361,294 B2 | 1/2013 | Wang | |
| 8,398,838 B2 | 3/2013 | Chen et al. | |
| 8,449,745 B2 | 5/2013 | Wang | |
| 8,480,874 B2 | 7/2013 | Henry | |
| D719,277 S | 12/2014 | Miller et al. | |
| D733,922 S | 7/2015 | Sjolander | |
| 9,234,874 B2 | 1/2016 | Panattoni | |
| D757,958 S | 5/2016 | Murray et al. | |
| 9,383,335 B2 | 7/2016 | Bjorkesten | |
| 9,400,260 B2 | 7/2016 | Suh | |
| D792,603 S | 7/2017 | Bulloch et al. | |
| 9,714,918 B2 | 7/2017 | Updyke | |
| D794,823 S | 8/2017 | Nelson | |
| D795,449 S | 8/2017 | Miller | |
| D806,894 S | 1/2018 | Nelson | |
| 2002/0079222 A1 | 6/2002 | Sevigny | |
| 2006/0163067 A1 | 7/2006 | Sevigny | |
| 2006/0278533 A1 | 12/2006 | Chen | |
| 2007/0205108 A1 | 9/2007 | Tzu-Chao et al. | |
| 2007/0284250 A1 | 12/2007 | Magnant | |
| 2011/0042213 A1 | 2/2011 | Updyke | |
| 2011/0042217 A1 | 2/2011 | Updyke et al. | |
| 2014/0045250 A1 | 2/2014 | Kreifels et al. | |
| 2016/0041123 A1 | 2/2016 | Guadagno | |
| 2016/0084797 A1 | 3/2016 | Goh et al. | |
| 2016/0258903 A1 | 9/2016 | Ran et al. | |
| 2017/0153204 A1 | 6/2017 | Bulloch | |

* cited by examiner

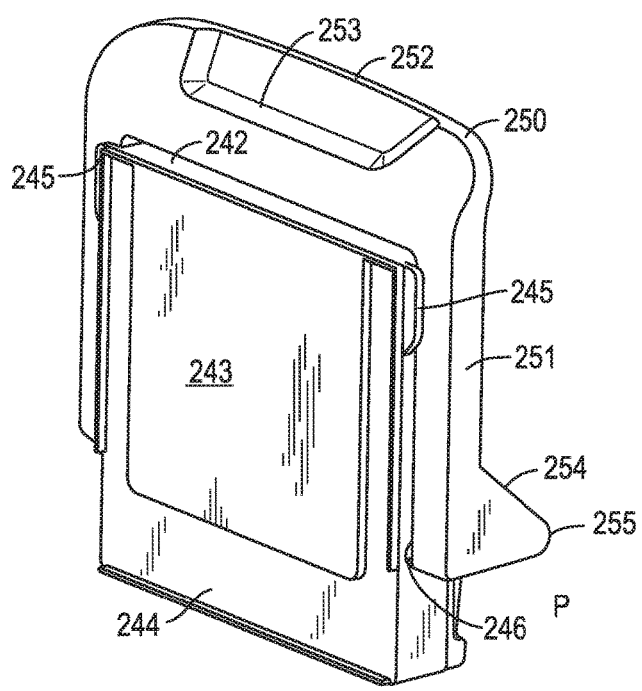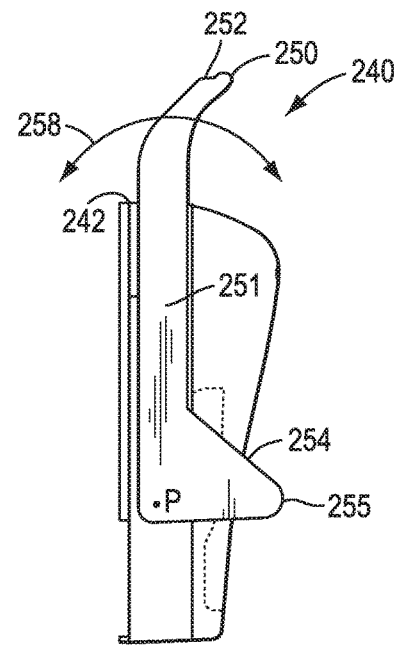
FIG. 9A  FIG. 9B
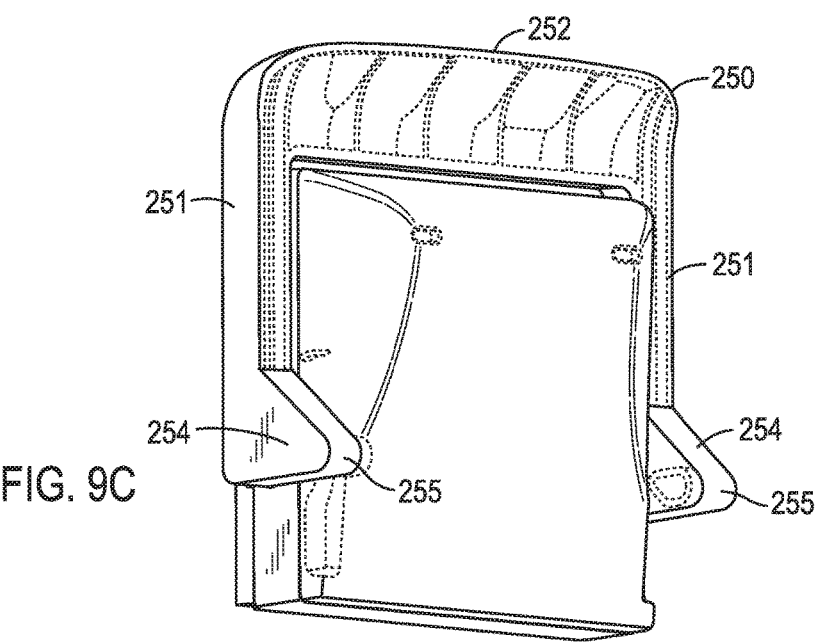
FIG. 9C

PREPARATION OF ELECTROPHORESIS GELS, AND RELATED DEVICES, SYSTEMS, AND METHODS

CROSS-REFERENCE TO RELATED APPLICATIONS

The present application claims the right of priority under 35 U.S.C. § 119(e) to U.S. Provisional Patent Appl. Ser. No. 62/255,050 entitled "Preparation of Electrophoresis Gels, and Related Devices, Systems, and Methods", filed on Nov. 13, 2015, which application is commonly owned with the present application and which the entire contents thereof are hereby expressly incorporated by reference in its entirety as though fully set forth herein.

TECHNICAL FIELD

The present disclosure relates to devices, systems, and methods for electrophoresis gel preparation. In particular, the present disclosure relates to devices, systems, and methods of electrophoresis slab gel preparation using, for example, polyacrylamide gels.

INTRODUCTION

Gel electrophoresis is a common procedure for the separation of biological molecules, such as deoxyribonucleic acid (DNA), ribonucleic acid (RNA), polypeptides, and proteins. In gel electrophoresis, the macromolecules are separated into bands according to the rate at which an imposed electric field causes them to migrate through a filtering gel.

The gel, typically formed and held in some type of containment structure, has an open molecular network structure defining pores that are saturated with an electrically conductive buffered solution. These pores through the gel are large enough to admit passage of the migrating macromolecules. During electrophoresis, the gel is placed in contact with one or more buffer solutions that provide electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known size, the size of other macromolecules can be determined.

Although there are various ways a gel can be formed and contained in a structure to perform electrophoresis, slab gels have been widely adopted in many applications. In such forms, the gel is sandwiched as a slab between two transparent plates, generally made of glass or plastic. The plates with the gel held between them are sometimes referred to as a gel cassette. Slab gels can provide the ability to analyze multiple samples simultaneously due to the width of the slab. The format permits multiple lanes to be fairly well separated across the width of the slab and the bands corresponding to each observed macromolecule in each sample down the columns associated with each lane, for example by autoradiography, fluorescent detection, colorimetric staining or other observation.

Gels can be cast and prepared as needed, sometimes referred to as "pour-your-own." Alternatively, they can be precast and provided to end users who will use them later in time from when they were initially cast. In either instance, the gel is initially poured as a liquid between the plates of the gel cassette and allowed to polymerize. To achieve distinguished lanes of different migrating samples during electrophoresis, a well-forming comb device can be inserted in the top edge of the poured liquid between the plates so that multiple individual test wells that ultimately align with what becomes the lanes of the gel are formed during polymerization.

Upon completion of polymerization, the gel cassette can then be transferred to an electrophoresis device and electrically coupled through a buffer medium, for example, held in a tank, to electrodes, such as an anode and a cathode for example, to perform electrophoresis.

The preparation of a slab gel and its ultimate use in electrophoresis involves multiple steps. There exists a need to offer devices, systems, and techniques to facilitate the process of preparing and using electrophoresis slab gels. There also exists a need to provide devices, systems, and techniques for electrophoresis slab gel preparation in a leak-free manner that produces high quality gels while minimizing the difficulty, number of steps, and components for preparation and use. Further, there exists a need to provide devices, systems, and techniques to prepare a gel having configurations that can be used with currently existing electrophoresis systems.

SUMMARY

In accordance an exemplary embodiment of the present disclosure, an apparatus for forming an electrophoresis slab gel may include a first plate and a second plate, each of the first and second plates having an inner face and an outer face. The apparatus may further include a spacer mechanism separate from each of the first and second plates, the spacer mechanism configured to be positioned between the inner faces of the first plate and the second plate, and along aligned side and bottom edges of the first and second plates. When subjected to a clamping force exerted on the outer faces of the first and second plates, the spacer mechanism is configured to maintain a separation distance between the inner faces of the first and second plates, and provide a seal to prevent leakage of an electrophoresis gel solution introduced between the plates.

In accordance with another exemplary embodiment, the present disclosure contemplates an apparatus for preparation of an electrophoresis slab gel that comprises a base having an opening configured to receive a cassette configured to contain an electrophoresis slab gel, a clamping mechanism configured to move relative to the base between an open position in which the clamping mechanism permits insertion of a cassette into the base, and a closed position in which the clamping mechanism is configured to clamp a cassette received in the base, a compressible pad operatively coupled to the clamping mechanism in a position to compress against a cassette received in the base in the closed position of the clamping mechanism. In yet another exemplary embodiment, the present disclosure contemplates a device for loading of sample into an electrophoresis slab gel that comprises a plurality of spaced apart teeth disposed to form a comb structure and a wedge-shape member extending from the comb structure in a direction opposite to a direction in which free ends of the plurality of teeth extend, the wedge-shape member terminating in an edge configured to trim the electrophoresis gel. The device is configured to mate with the cassette in a manner to position the teeth of the comb structure laterally across the cassette, the spaces between adjacent teeth being configured to define electrophoresis lane guides for loading sample into the gel of the cassette.

In another exemplary embodiment, the present disclosure contemplates a method of preparing an electrophoresis slab gel that comprises positioning two aligned transparent plates with a spacer mechanism sandwiched between the plates into a support base while the support base is in a first position; moving a clamping mechanism relative to the support base to exert a force against the plates sufficient to clamp the plates and the spacer mechanism in a fixed position relative to the base, wherein the force of the clamping mechanism is sufficient to seal the spacer mechanism against the plates to prevent leakage of an electrophoresis gel solution introduced between the plates. The method further may comprise tilting the support base with the clamped plates and spacer mechanism at an angle relative to the first position of the support base; and with the support base tilted, loading a polymerizable electrophoresis gel solution into a cavity defined between the clamped plates and spacer mechanism. After the loading, the method comprises placing the support base in the first position and allowing polymerization of the loaded electrophoresis gel solution.

In another exemplary embodiment, the present disclosure contemplates a kit for preparing an electrophoresis slab gel, the kit comprising a first plate and a second plate, each of the first and second plates having an inner face and an outer face; a spacer mechanism separate from each of the first and second plates, the spacer mechanism configured to be positioned between the inner faces of the first plate and the second plate, and along aligned side and bottom edges of the first and second plates; a base having an opening configured to receive the first and second plates aligned with the spacer mechanism positioned between the inner faces of the first and the second plates; a clamping mechanism configured to move relative to the base between an open position in which the clamping mechanism permits insertion of the first and second plates with the spacer mechanism disposed therebetween, and a closed position in which the clamping mechanism is configured to clamp the first and second plates to seal against the spacer mechanism disposed therebetween; a compressible pad configured to be operatively coupled to the clamping mechanism so as to compress against the plates in the closed position of the clamping mechanism; a loading guide accessory tool comprising a plurality of spaced apart teeth disposed to form a comb structure and a blade member extending from the comb structure in a direction opposite to a direction in which free ends of the plurality of teeth extend; and ingredients for forming a polymerizable electrophoresis gel.

Additional objects and advantages will be set forth in part in the description which follows, and in part will be obvious from the description, or may be learned by practice of the present disclosure and exemplary embodiments. At least some of the objects and advantages will be realized and attained by means of the elements and combinations particularly pointed out in the claims.

It is to be understood that both the foregoing general description and the following detailed description are exemplary and explanatory only and are not restrictive of the present disclosure or claims, the latter of which should be entitled to their full breadth of scope, including equivalents.

BRIEF DESCRIPTION OF DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

FIGS. 9A-9C are various views of an exemplary embodiment of a clamping mechanism of the casting rig of FIG. 7 in a closed configuration;

DESCRIPTION OF EXEMPLARY EMBODIMENTS

Figure 1:
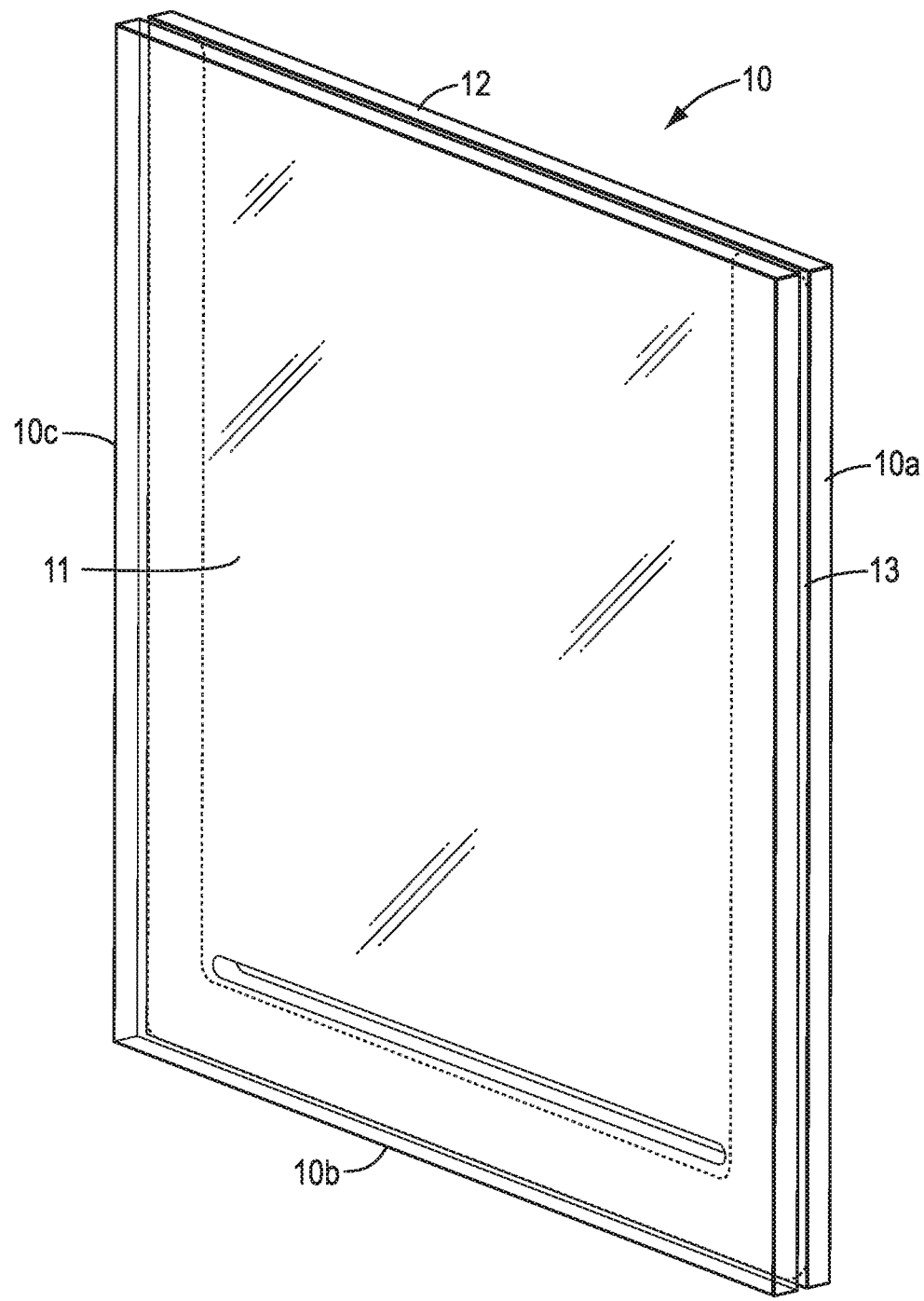
FIG. 1 is a front perspective view of an exemplary embodiment of a cassette for an electrophoresis slab gel in accordance with the present disclosure.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "bottom", "above", "top", "front", "rear", "side", and the like—may be used to describe one element's or feature's relationship to another element or feature as illustrated in the figures and in an orientation of the devices in normal use. These spatially relative terms are intended to encompass different positions (i.e., locations) and orientations (i.e., rotational placements) of a device in use or operation in addition to the position and orientation shown in the figures. For example, if a device in the figures is turned over, elements described as "bottom" or "beneath" relative to other elements or features would then be on "top" or "over" relative to the other elements or features. Thus, the exemplary term "below" can encompass both positions and orientations of above and below. A device may be otherwise oriented (rotated 90 degrees or at other orientations) and the spatially relative descriptors used herein interpreted accordingly.

Solutions used for use in preparing and using electrophoresis slab gels in accordance with various exemplary devices, systems, and methods described can include polyacrylamide or agarose type gels. Agarose gels have a relatively large pore size and are generally used for separating nucleic acids and protein complexes. Polyacrylamide gels have a relatively smaller pore size and are generally used for separating most proteins and smaller nucleic acids.

Polyacrylamide gels are generated by the polymerization of acrylamide monomers that are crosslinked into long chains by the addition of bifunctional compounds such as N,N,-methylenebisacrylamide ("bisacrylamide"), which react with free functional groups of the chain termini. The concentration of acrylamide and bisacrylamide determines the pore size of the gel. The higher the acrylamide concentration, the smaller the pore size, which results in resolution of lower molecular weight molecules and vice versa. Polyacrylamide gel electrophoresis (PAGE) provides desirable electrophoresis characteristics because the gels are optically transparent, electrically neutral, and can be made with a range of pore sizes.

Electrophoresis can be performed under native (non-denaturing) conditions and can also be performed under denaturing conditions by using an anionic detergent, such as sodium dodecyl sulfate (SDS). When polyacrylamide gel electrophoresis is used with sodium dodecyl sulfate, i.e. as SDS-PAGE, the charge density of the macromolecules is controlled by adding SDS to the system. SDS molecules associate with the macromolecules and impart a uniform charge density to them, substantially negating the effects of any innate molecular charge. The resultant SDS-macromolecule complexes are highly negatively charged, thereby conferring electrophoretic mobility, and are resolved in the gel based on their size, not charge.

SDS-PAGE gels compatible with the present exemplary embodiments include, but are not limited to, for example those developed by Ornstein and Davis (Ornstein, L. (1964) *Ann. NY Acad. Sci.*, 121: 321 and Davis, B. J. (1964) *Ann. NY Acad. Sci.*: 121: 404), and modified for use with SDS by Laemmli (Laemmli, 1970, *Nature* 227, 680-686). The Laemmli buffer system includes of 0.375 M tris (hydroxymethyl) amino-methane ("Tris") titrated to pH 8.8 with HCl in the separating gel. The stacking gel consists of 0.125 M Tris, titrated to pH 6.8. The anode and cathode running buffers contain 0.024 M Tris, 0.192 M glycine, 0.1% SDS (i.e. as a "Tris-glycine buffer"). Note that use of the present exemplary embodiments are not limited to just these gel types. Rather, a variety of gel formulations may be prepared using the devices, systems, and techniques disclosed, including but not limited to, for example, Bis-Tris, Bis-Tris Plus, Tris-Glycine/Threonine, Tris-Acetate, Tricene, TBE-Urea, NativePAGE, and isoelectric focusing (IEF), Zymogram and other gel formulations.

Gels also may be referred to as continuous or discontinuous. A continuous gel is a gel that has been formed from a single acrylamide solution in the entire electrophoresis gel apparatus, e.g., gel cassette, whereas a discontinuous gel is formed from two or more acrylamide solutions: (1) a small, low-concentration stacking gel where the macromolecule wells reside, and (2) a larger portion of the gel wherein protein separation occurs. In the traditional Tris-glycine electrophoresis gel system, the macromolecules are stacked in the stacking gel between the highly mobile leading chloride ions (in the gel buffer) and the slower trailing glycine ions (in the running buffer). The reason for using the stacking gel is to improve the resolution of the bands in the gel. The stacked macromolecule bands undergo sieving once they reach the separating gel.

Use of an approximately ph-neutral gel and buffer system also may be used in conjunction with various exemplary embodiments described herein. Suitable formulations are disclosed, for example, in U.S. Pat. No. 8,945,360 B2, issued Feb. 3, 2015, and in U.S. Provisional Application No. 62/241,642, entitled "ELECTROPHORESIS GEL WITH EXTENDED SHELF LIFE AND HIGH PERFORMANCE," filed Oct. 14, 2015, both of which are incorporated by reference herein.

Figure 2:
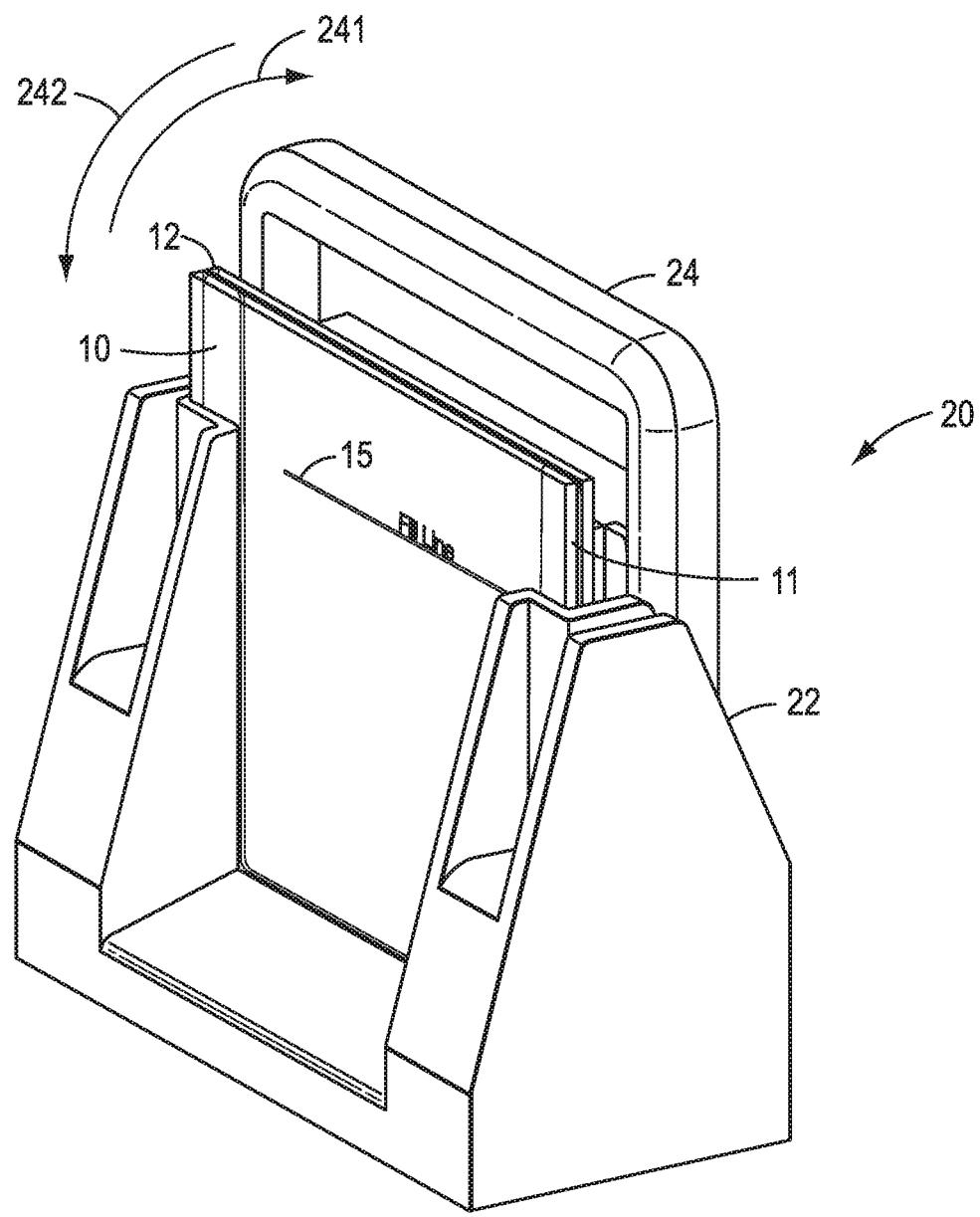
FIG. 2 is a perspective view of a casting rig holding a cassette for preparing an electrophoresis slab gel in accordance with the present disclosure.

In accordance with various exemplary embodiments, a system for preparing an electrophoresis slab gel can include one or more of the components illustrated in FIGS. 1-3. With reference to FIG. 1, a gel cassette 10 that includes a front plate 11 and a back plate 12 of generally the same overall outer dimensions are configured to be placed together in an aligned manner as illustrated. A spacer mechanism can be positioned between the plates 11 and 12 so as to separate them by a distance, thereby providing a cavity between the plates that allows the gel to be formed between them. For example, one or more spacers 13 may be provided around one or more edges 10a-10c of the plates 11 and 12, sandwiched therebetween in the formed gel cassette. In various exemplary embodiments, the spacer mechanism may be configured to separate the plates 11 and 12 by a distance ranging from about 0.75 to about 1.5 millimeters. Although it may be desirable to provide a spacer mechanism around one or more of the bottom and side edges 10a, 10b, 10c, those having ordinary skill in the art would appreciate that other positions for spacers can be used, such as for example, in corner regions of the plates 11, 12, or discontinuously along the edges 10a, 10b, 10c. As will be appreciated from the description further below, in an exemplary embodiment in which a discontinuous spacer mechanism is used that does not extend around the entirety of the edges 10a-10c, other sealing structures may be employed to seal the cassette against leakage of the gel solution when introduced into the cassette cavity. For example, a cassette may be provided that uses a weld or other adhesive to provide a seal around the edges of the two plates 11, 12.

To permit observation of the dye migration during electrophoresis, in various exemplary embodiments the plates 11, 12 are transparent. For example, the plates 11, 12 may be made of glass, such as, for example, borosilicate (Pyrex®) or soda lime glass, or clear plastic, such as, for example, styrene acrylonitrile resin (SAN), polyethylene terephthalate (PET), polycarbonate (PC), acrylonitrile butadiene styrene (ABS). In an exemplary embodiment, the glass or plastic may optionally be coated with an additional material, for example to provide a non-stick surface and/or oxygen barrier.

To stabilize the cassette and free up an individual's hands during pouring of the liquid gel-forming solution into the cassette when casting the gel, a casting rig may be used. FIG. 2 depicts an exemplary embodiment of a casting rig 20, shown with the cassette 10 received in the rig 20 in position to allow the contents for forming the gel to be loaded (poured) into the top of the cassette 10 between the plates 11, 12, as described above. The casting rig 20 may be in a variety of forms but generally includes a base 22 to support the cassette 10 on a work surface, for example, a horizontal work surface. The base 10 is configured so as to permit visibility of the cassette 10 over a large majority of the front face of the plate 11, for example, so as to be able to view a width and length over the front face of the plate where the lanes of the gel will be formed during electrophoresis.

In an exemplary embodiment of the present disclosure, the casting rig 20 uses a clamping mechanism to secure the cassette 10 in the rig 20. For example, the casting rig 20 can include a releasable handle and clamping plate combination 24 configured to interact with the base 22 to clamp the cassette 10 between the base 22 and the handle/clamping plate 24. The handle portion of the handle and clamping plate combination 24 may be generally movable (e.g., rotatable) relative to the base 22 in directions 241 and 242, respectively, to an open position (not shown) allowing insertion/removal of the cassette 10 between the clamping plate and upright portions 23 of the base 22 and a closed position (shown) in which the handle and clamping plate 24 clamps the cassette 10 in position against the uprights 23 of the base 22. Various mechanisms can be used to provide a sufficiently secure clamping force of the handle and clamping plate combination 24 and base 22 against the cassette 10 in the closed position. For example, the handle and clamping plate 24 may be biased, such as, for example, spring-biased in the clamped position. In this case, the handle portion can be moved to the open position against the spring force. In another exemplary embodiment, a set screw mechanism (e.g., quarter-turn screw) accessible from the back of the rig 20 could be used to permit a handle and clamping plate combination to move generally forward and backward relative to the cassette 10 and base 20 so as to permit sufficient clamping of the cassette 10. In yet another exemplary embodiment, the clamping mechanism may be a hinged door with a latch mechanism to place the clamping plate (door) in the open and closed (clamping) configurations. Yet another exemplary embodiment could employ a one or more clamps configured to clamp onto the front and rear plates to clamp the cassette around its edges. Other exemplary embodiments are discussed further below.

Figure 3A:
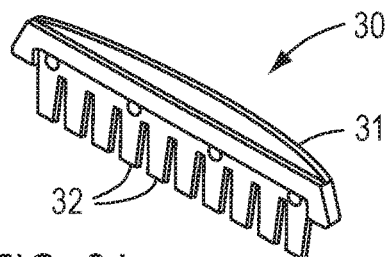
FIGS. 3A and 3B show an exemplary embodiment of an accessory comb in isolation and inserted in a gel cassette in accordance with the present disclosure.
Figure 3B:
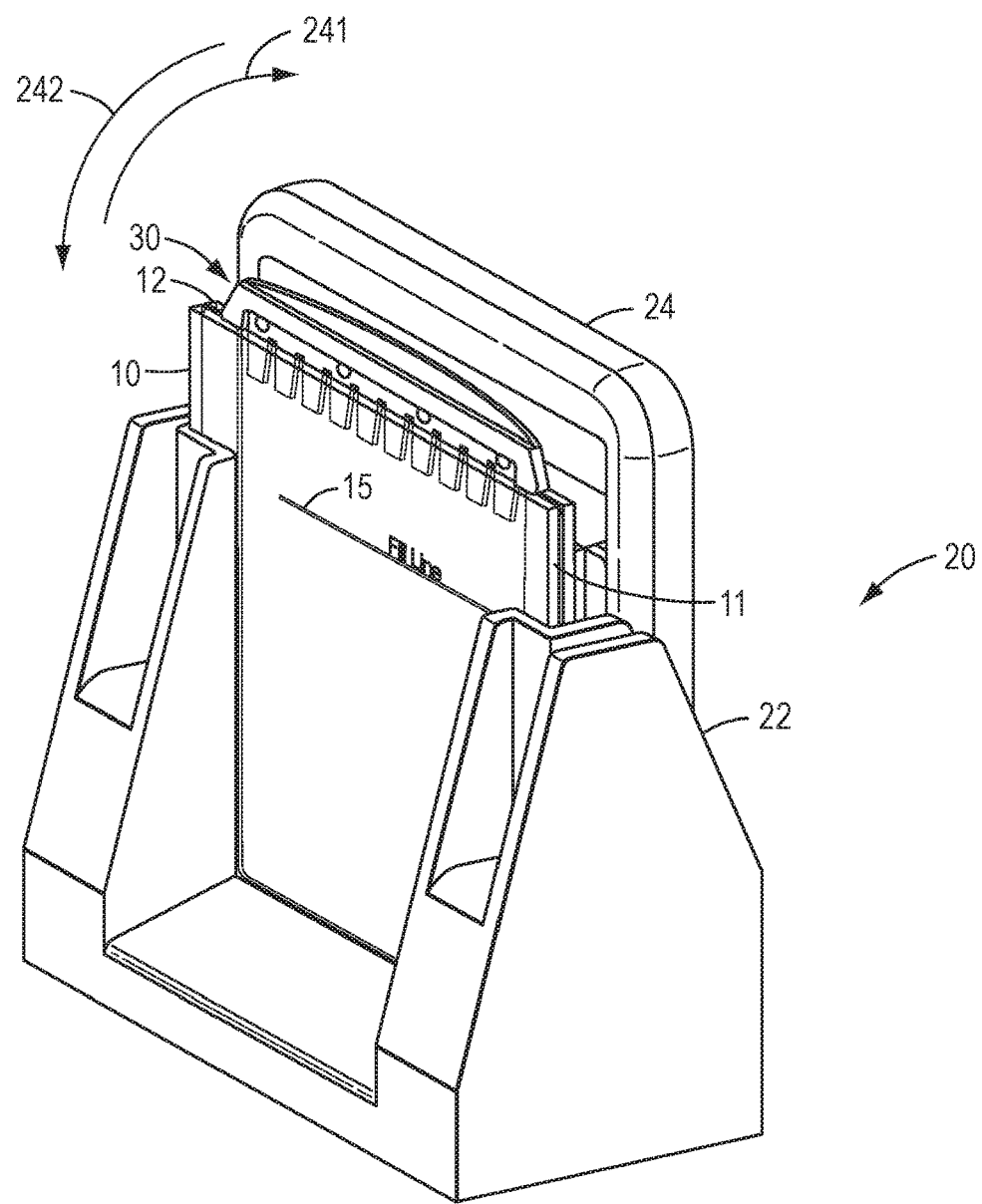

To assist in loading sample into well-delineated and uniformly spaced lanes of the formed gel in the cassette, a system for electrophoresis slab gel preparation can include an accessory tool configured to define wells in the formed gel. FIGS. 3A and 3B show one exemplary tool generally configured as a comb 30 in isolation (FIG. 3A) and in position in the cassette 10 (FIG. 3B) after the solution for forming the gel has been poured and before polymerization of the gel. The comb 30 includes a grasping edge 31 and a series of teeth 32 extending from the grasping edge 31. The teeth 32 are inserted in the gel in the cassette 10 and permit observation of an outline of "wells" in the otherwise substantially transparent slab gel in the cassette 10. Accordingly, the thickness of the teeth should approximate the thickness of the spacer mechanism to permit the comb to be inserted between the plates 11, 12. Upon removal of the comb 30, an upper portion of the slab gel includes wells formed in the gel where the teeth were. This enables loading of the sample generally at each of the teeth 32/wells, which are spaced so as to form well-delineated and substantially uniformly spaced lanes during electrophoresis. Any number of teeth may be utilized as desired and depending on the number of lanes desired and/or size of the overall cassette 10. The comb 30 may include any number of teeth. In various exemplary embodiments, a comb may include from 1 to 20 teeth, such as, for example, 10, 12, 15, or 17 teeth so as to form 10, 12, 15, or 17 wells in the slab gel. Combs in accordance with various exemplary embodiments may be made from a variety of materials, such as, for example, plastic, for example, a polycarbonate.

Figure 4:
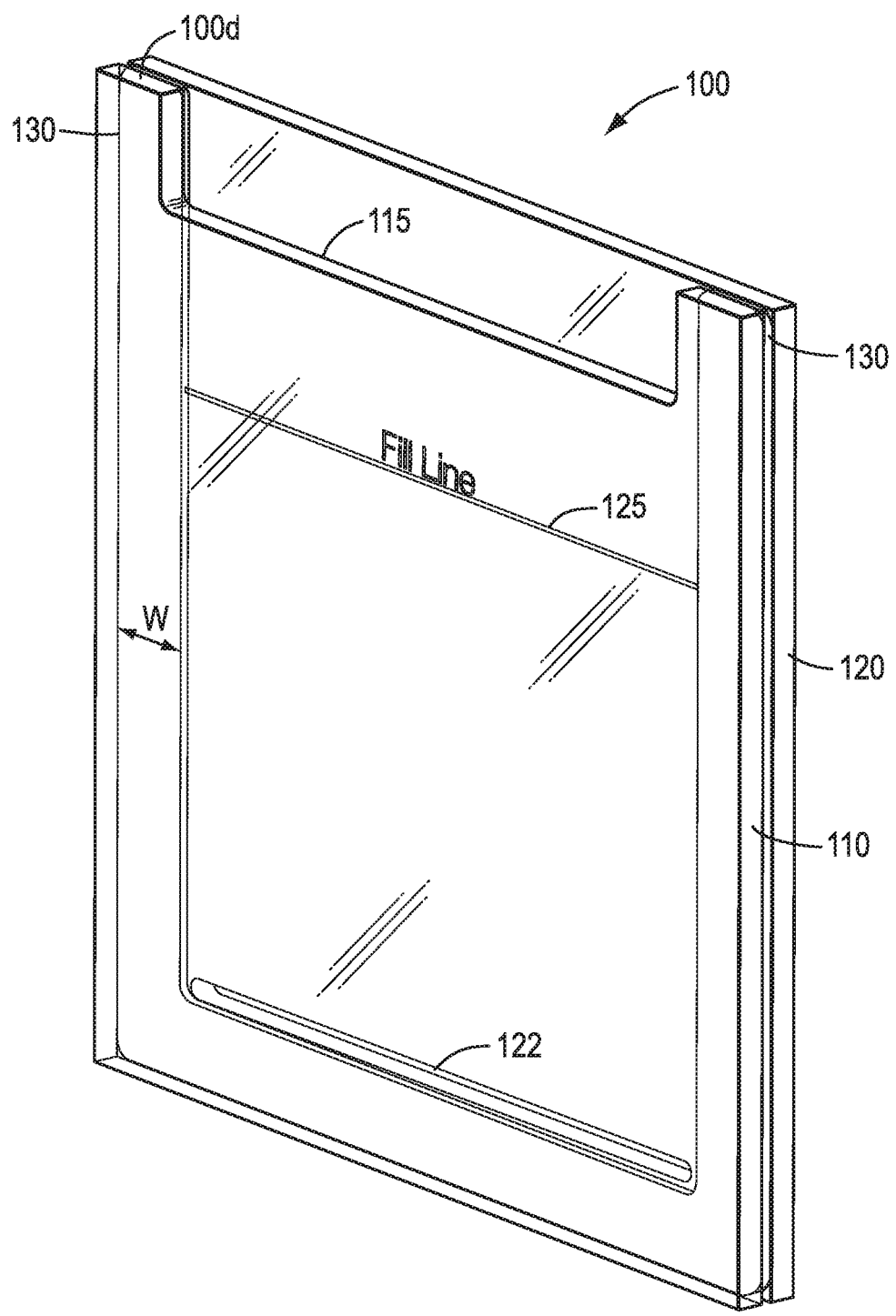
FIG. 4 is a front perspective view of another exemplary embodiment of a cassette for an electrophoresis slab gel in accordance with the present disclosure.
Figure 5:
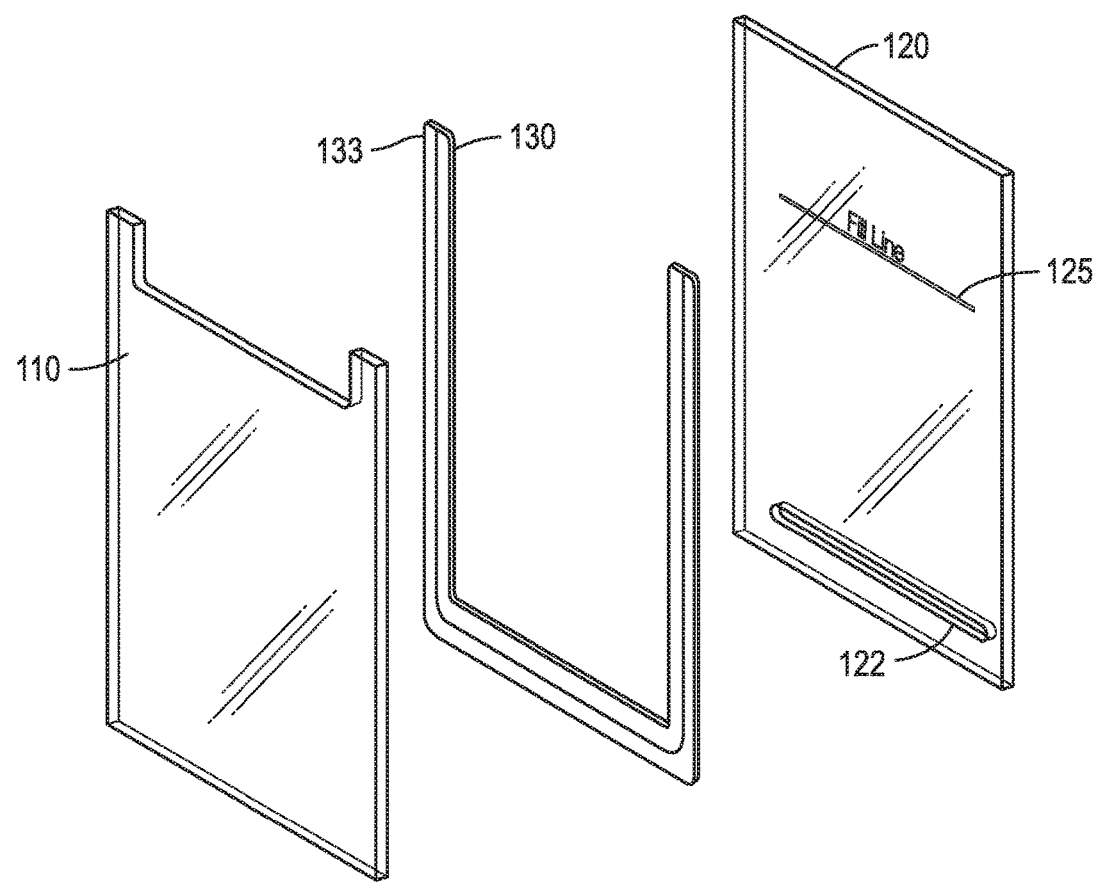
FIG. 5 is an exploded view of the cassette of FIG. 4.
Figure 6:
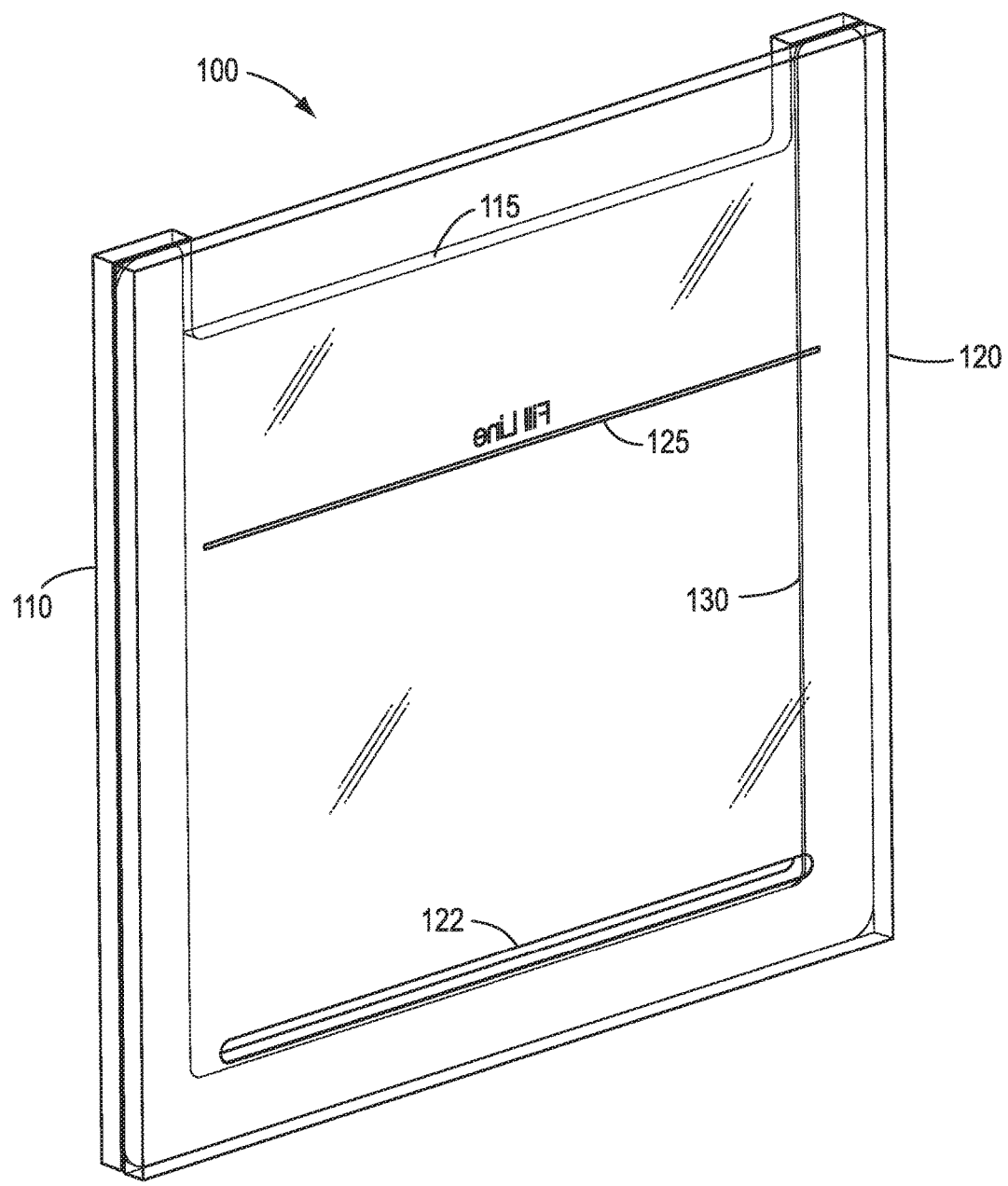
FIG. 6 is a back perspective view of the cassette of FIG. 4.

With reference now to FIGS. 4-6, another exemplary embodiment of a cassette for receiving the gel casting solution and permitting it to polymerize to form a slab gel is depicted. FIG. 4 shows a front perspective view of the cassette 100, FIG. 5 shows an exploded view of the cassette 100, and FIG. 6 shows a back perspective view of the cassette 100. Similar to the cassette 10 described above, the cassette 100 has a front plate 110 and a back plate 120 of the same overall dimensions so as to align with each other when positioned to form the cassette 100, as depicted in FIGS. 4 and 6. Between the plates 110 and 120 is a spacer mechanism 130 that is configured to extend along the side and bottom edges of the plates 110 and 120. As depicted, in an exemplary embodiment, the spacer mechanism 130 is generally U-shaped.

As discussed above, the plates 110 and 120 are transparent and can be made of plastic or of glass, such as, for example borosilicate or soda lime glass. The spacer mechanism 130 may be a rigid material or an elastomeric material, such as, for example silicone or other suitable material. In various exemplary embodiments, the spacer mechanism 130 has a durometer ranging from about 40 A to about 80 A. Higher durometers may improve handling by being less floppy, but a higher clamping force may be required to seal against the cassette plates. The sides and legs of the spacer mechanism 130 have a relatively small width dimension w so as to provide an open area sufficient for a plurality of lanes in the electrophoresis gel to be formed between the right and left sides of the spacer mechanism 130. For example, the width dimension should be chosen to generally not protrude beyond the edges of the plates 110, 120 and to permit a plurality of lanes to span the opening between the right and left side legs of the spacer mechanism 130. Those of ordinary skill in the art would appreciate that any number of lanes may be provided as desired and depending on the overall opening size between the right and left side legs of the spacer mechanism. In various exemplary embodiments, there may be from 1-20 lanes, such as for example, 10-17 lanes, for example, 10, 12, or 15 lanes which may each range from about 1 mm to about 70 mm in width. In various exemplary embodiments, the lanes may each have width ranging from about 2.9 mm to about 4.6 mm.

In various exemplary embodiments, the thickness of the spacer mechanism 130 can range from about 0.75 mm to about 1.5 mm, thereby providing such spacing between the inner facing surfaces of the front and back plates 110, 120 to provide room for and corresponding thickness of the slab gel. Accordingly, when the plates 110, 120 and spacer mechanism 130 are sandwiched together, as illustrated in FIG. 4, a cavity between the plates 110, 120 and bound by the spacer mechanism 130 is defined that can receive the gel-forming solution and provide a slab gel after polymerization. In general, the thickness of the spacer mechanism can be selected so as to achieve a desired gel thickness. In various exemplary embodiments, the thickness of the cassette plates also may be altered depending on the thickness of the spacer mechanism, desired gel thickness, and/or use of the cassette in various electrophoresis systems, such as, for example, existing electrophoresis systems that are configured to receive a specified overall dimensioned cassette format. Those having ordinary skill in the art would appreciate how to adjust the thickness of the spacer mechanism and/or the cassette plates based on the present disclosure.

When a clamping force is provided on the plates 110, 120, the material of the spacer mechanism 130 enables the spacer mechanism 130 to provide a seal around the edges of the plates 110, 120, and thus the cassette 100. In an exemplary embodiment, the spacer mechanism 130 includes a stepped surface, shown as 133 in FIG. 5, on one or both of the front and back surfaces of the spacer mechanism 130. The stepped surface can be configured such that the inner portion of the spacer mechanism 130 has a slightly greater thickness than the outer portion. In this way, a clamping force used to create the seal of the plates 110, 120 with the spacer mechanism 130 can be reduced due to the reduction in contact area of the spacer mechanism 130 with the plates 110, 120, resulting in a higher sealing pressure occurring when subject to a given clamping force.

When a stepped profile of the spacer mechanism 130 is utilized, surface portions either outside the step or inside the step can be in contact with the plates 110, 120. However, separation of the plates 110, 120, for example to recover the formed gel, may be facilitated in an exemplary embodiment wherein the stepped profile is configured such that only surface portions of the spacer mechanism 130 inside of the step are in contact with the plates 110, 120 when the cassette is assembled.

Although in an exemplary embodiment, it is contemplated that the spacer mechanism 130 could be formed as part of or secured to one of the plates 110, 120, providing the spacer mechanism 130 as a separate part sandwiched between and not otherwise adhered to the plates 110, 120 can facilitate intact removal of the formed slab gel. In addition, replacement of the spacer mechanism 130, if needed, may be easier when the spacer mechanism is provided as a free and separate part not adhered to either of the plates 110, 120. In various exemplary embodiments, the spacer mechanism 130 can be molded, and also may be provided with a surface texture, via molding or other surface treatment. Such texturing can assist in preventing the spacer mechanism from sticking to the cassette plates and/or promote accurate alignment and placement of the spacer mechanism with relation to the outer edges of the plates. Texturing may be selected so as to ensure a sufficient smoothness of the surface of the sealing mechanism is retained in order to establish a leakproof seal with the plates can be maintained.

As discussed with reference to the embodiment of FIG. 1, in the cassette 100 of FIG. 4, the front plate 110 has a cut out portion 115 at a top edge of the front plate 110. The cut out portion 115, as will be explained further below, provides a shoulder for resting an accessory comb tool used to provide wells for sample loading and/or other accessory tools as further described below. In an exemplary embodiment, the cut out portion has a width (lateral) dimension approximately equal to the distance between the inner edges of the right and left legs of the spacer mechanism 130, and has a length dimension ranging from about 2 mm to about 30 mm, for example about 11.6 mm. The length of the cut out region may be selected so as to promote desired resolution of the formed gel, in particular when using a comb inserted in the gel to form wells.

In the exemplary embodiment of FIGS. 4-6, the back plate 120 of cassette 100 has a slot opening 122 that extends through the thickness of the plate 120 to provide access to the gel to pass electrical current therethrough during electrophoresis. The slot opening 122 can have an overall size and placement so as to make it compatible with existing electrophoresis slab gel systems in which the slot opening 122 communicates with an anode buffer chamber. Such electrophoresis slab gel systems may include, but are not limited to, for example, XCell SureLock™ Mini Cell electrophoresis system from Thermo Fisher Scientific. In an exemplary embodiment, the slot opening 122 can be provided about 10 mm from a bottom edge of the plate and can extend laterally such that its ends terminate about 10 mm from side edges of the plate. In addition, during pouring of the gel, the slot opening 122 is configured to fill with liquid.

To assist in separation of the plates 110, 120 and ease of removal to provide an intact gel after electrophoresis, the slot opening 122 can be formed with draft angles (not shown in the figures) that taper inwardly from the surface of the plate 120 in contact with the gel to the opposite (outer) surface of the plate 120. The draft angles also can facilitate cleaning of the slot opening 122 surfaces.

Although the slot opening 122 in the exemplary embodiments illustrated is disposed on the back plate 120, those having ordinary skill in the art would appreciate that a slot opening in addition to or in lieu of the slot opening 122 on the back plate 120 may be provided on the front plate 110, with appropriate modifications made to other system components to perform electrophoresis and formation of the electrophoresis gel.

In various exemplary embodiments, a cassette for forming and containing an electrophoresis slab gel in accordance with the present disclosure also can be provided with a marking or other indicia to identify a desired fill level during pouring of the gel-forming solution. For example, the cassette may include a fill level indicator, which may be a permanent marking or other indicia provided on the cassette. In the exemplary embodiment of FIGS. 4-6, the cassette 100 is provided with a line 125 across a portion of the cassette 100 at a position along its length that corresponds to a desired fill level of the gel-forming solution during pouring of the same to form the gel. For example, the fill line 125 may be placed about 22 mm to about 50 mm, such as for example about 32.5 mm from the top edge of the 100d of the cassette. In embodiments wherein a comb is used to form wells in the gel, the fill line can be positioned about 1 cm below where the bottom of the comb, and thus formed wells, are positioned. Such positioning may provide a desired level of a resolving gel and additional room above the desired fill level for a stacking gel. The fill line 125 can be provided alone or in conjunction with other indicia, such as, for example, text as shown denoting it as a fill line.

The indicia, such as the line 125 and/or corresponding text or other symbols, denoting the desired fill level may be provided by laser etching, screen printing, or the like, and may be provided on either or both of the front plate 110 and the back plate 120. To avoid interference with the formation of the gel and/or undesirable sticking during separation of the plates 110, 120 and slab gel recovery, it is desirable to provide the markings on the outside surfaces of one or both of the front and back plates 110, 120 that do not come into contact with the gel. In addition, the indicia, when provided on a plate, such as the back plate 120, with the slot opening 122 can assist in orienting the plate so that the draft angle of the slot opening 122 is oriented correctly relative to the gel. For example, as indicated in FIG. 6, if writing is included as part of the indicia, then the mirror image of the writing can be etched or otherwise formed on the surface of the back plate 120 intended to face outwardly away from the gel, since it will be oriented correctly when viewed through the transparent front plate 110 of the cassette 100. In this way, the indicia can serve as a mechanism by which a proper orientation of the plates in terms of which surface should be placed in contact with the gel can be determined, in particular so as to properly orient the draft angle of the slot opening 122 so as to facilitate removal of the slab gel. Aside from using the orientation of the writing, a tactile sensation of the indicia can be provided to indicate the surface of the plate 110, 120 to face outward and away from the gel.

In lieu of, or in addition to, placing indicia for a desired fill level on the cassette 100, such indicia can be provided on the casting rig, such as, for example, on a clamping mechanism of the rig of various exemplary embodiments described herein. FIG. 2 illustrates an exemplary positioning of indicia in the form of a fill line 15 positioned on a clamping plate 24 of the casting rig 20, with the fill line 15 being visible through the transparent plates of the cassette. Those of ordinary skill in the art would appreciate that other arrangements and types of indicia can be used to indicate a desired fill level when pouring the gel and the exemplary embodiments depicted should not be considered as limiting.

Figure 7:
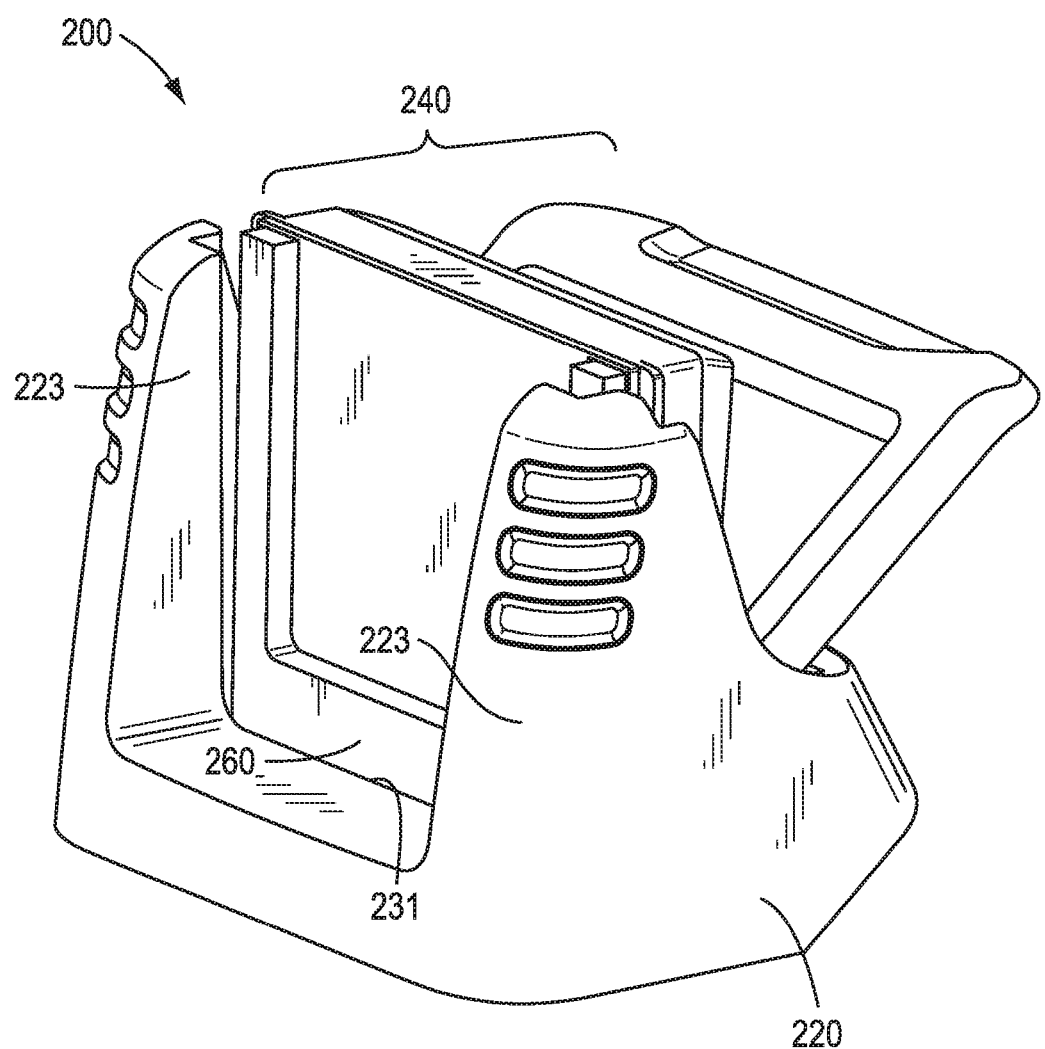
FIG. 7 is a front perspective view of an exemplary embodiment of an electrophoresis gel casting rig in accordance with the present disclosure.

Turning now to FIGS. 7-12, another exemplary embodiment of a casting rig, and components thereof, for holding the cassette during casting of the gel is illustrated. The casting rig 200 is an assembly comprising as main components a rig base 220, a movable clamping mechanism 240, and an elastically compressible sealing pad 260. As illustrated in FIG. 7, without a cassette inserted in position in the rig 200, the movable clamping mechanism 240 tends toward an open position in the absence of any other force acting on the clamping mechanism 240. In the open position illustrated, the clamping mechanism 240 provides a sufficient space between uprights 223 of the rig base 220 to permit a cassette (not shown in FIG. 7) to be inserted in the rig 220 between the uprights 223 and the clamping mechanism 240. The clamping mechanism 240 is a separate component that can be inserted and removed from the rig base 220, which can facilitate cleaning of the entire rig assembly 200, although the present disclosure contemplates embodiments wherein the clamping mechanism and base are attached. The sealing pad 260 can be provided as a separate component and/or may be configured to be secured, such as via adhesive, to the clamping mechanism 240. In either case, the sealing pad 260 may be replaceable if the pad begins to deteriorate or lose its compressibility after repeated use.

Referring now to FIGS. 8A-8D, a front perspective, rear perspective, front plan, and side view of the rig base 220 are depicted. The rig base 220 has a relatively wide-bottomed end portion 224 having a surface configured to rest flatly on a surface during use of the rig 220 for pouring an electrophoresis gel cassette. The surface may be a continuous solid surface or, as shown, may be a plurality of ribs in the case of a molded rig base. Extending upwardly from each side of and generally perpendicularly to the wide-bottomed end portion 224 are the upright portions 223. Thus, the upright portions 223 and the wide-bottomed end portion 224 together form an approximate U-shape, providing a relatively large opening 226 configured to permit the majority of the face of a gel cassette to be viewed when received in the casting rig 200. The end portion 224 further is configured to present a concave, trough-like surface extending between the upright portions 223. This surface can be useful for collecting any leakage of gel-forming solution that may occur during preparation of the gel or otherwise.

Figure 8A:
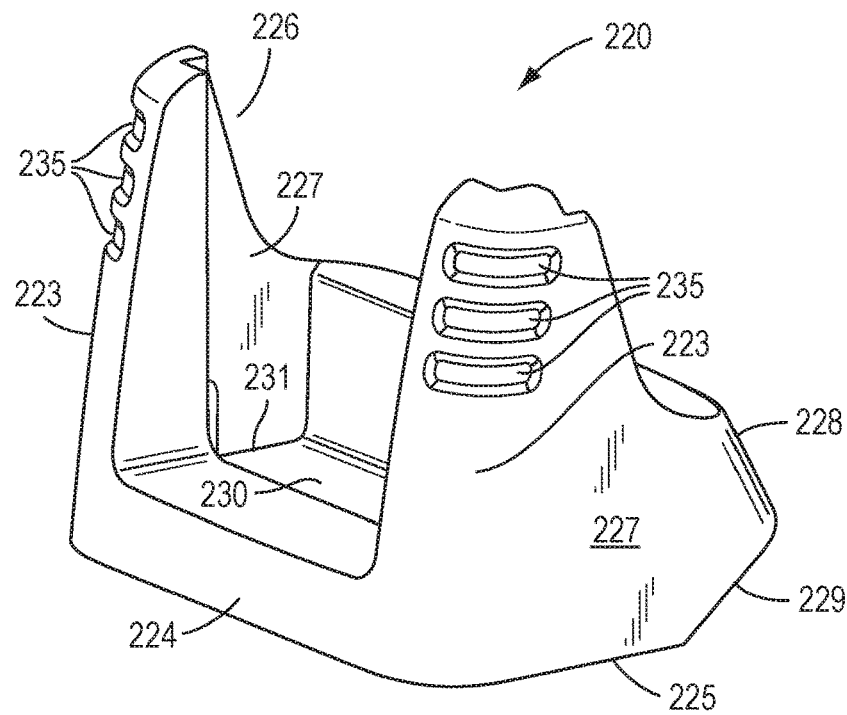
FIGS. 8A-8D are various views of an exemplary embodiment of a base of the casting rig of FIG. 7.

The upright portions 223 wrap around to form side walls 227 of the rig base 220, with the side walls 227 each having a generally sloped profile from the free end (top) of the upright portions 223 toward the wide-bottomed end portion 224. Connecting the side walls 227 laterally across the back of the rig base 220 (i.e., across the rig base 220 generally opposite to the U-shaped connection provided between the upright portions 223 and the wide-bottomed end portion 224) is a rear wall 228. The rear wall 228 is disposed at a height located between the wide-bottomed end portion 224 and the free ends (top) of the upright portions 223, and the bottom of the rear wall 228 connects to the bottom surface of the wide-bottomed end portion by a sloped surface 229. As will be discussed further below, the sloped surface 229 provides a sufficient surface area to allow the rig base 220 to rest on the sloped surface 229 (see FIG. 16), in which position, pouring the gel can be facilitated. Aside from the side walls 227 and rear wall 228, the rig base 220 is open from the top and back of the rig base 220 to permit relatively unimpeded insertion and removal of the clamping mechanism 240 and sealing pad 260. As best shown in FIG. 8A, the rig base 220 includes an interior bottom support surface 230 to receive and support a cassette and clamping mechanism 240. The interior bottom support surface 230 is recessed between the rear wall 228 and a front ledge 231 extending from the wide-bottomed end portion 224 that forms part of the U-shaped connection with the upright portions 223.

Figure 8B:
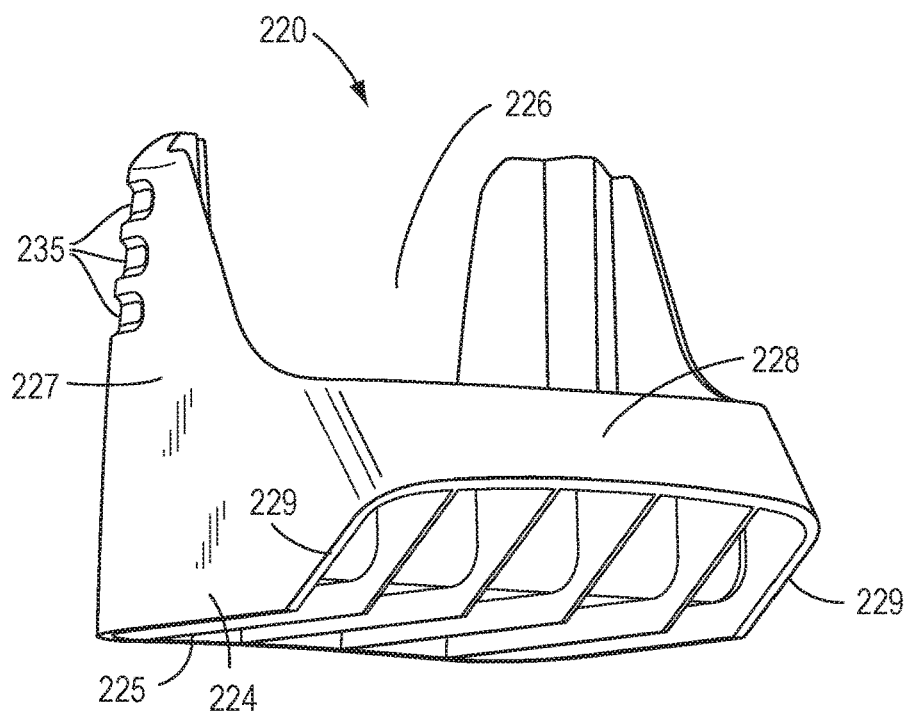
Figure 8C:
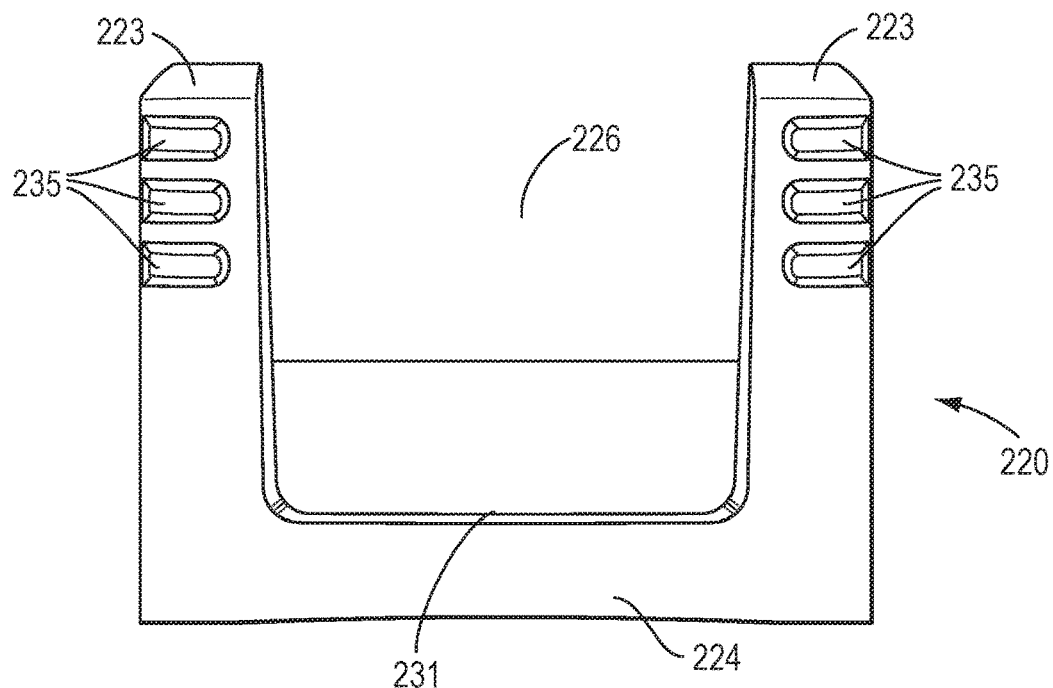
Figure 8D:
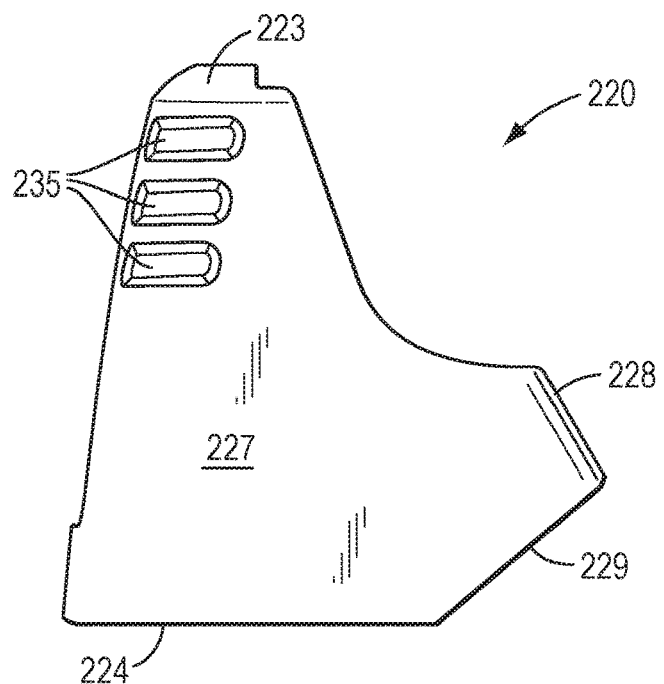

As will be further appreciated when the interaction between the clamping mechanism 240 and rig base 220 is described below, an interior surface of the upright portions 223 includes a vertically extending stepped profile, shown best in FIGS. 8A, 8B, and 8D that provide differing surfaces that interact with the clamping mechanism 240 and a gel cassette in the closed position of the clamping mechanism 240.

To assist in handling of a rig assembly, various exemplary embodiments of a casting rig may include gripping surface features provided on one or more parts of the casting rig. By way of non-limiting example, a series of grooves 235 are shown on the upright portions 223 of the rig base 220 in FIGS. 8A-8D. The grooves 235 are positioned toward the free ends of the upright portions 223 so as to provide a conveniently located area for a user's thumb and forefinger to grasp the rig base 220. Those having ordinary skill in the art would appreciate that the gripping surface features configuration and arrangement can take a variety of forms without departing from the scope of the present disclosure and claims, including but not limited to, for example, surface roughening, knurling, friction pads, etc. and have other locations in order to facilitate handling of a casting rig.

Various materials may be used to make the rig base 220. To permit reuse, the materials used to make the rig base 220 should provide surfaces that can be relatively easily cleaned. In various exemplary embodiments, the rig base 220 can be made of plastic and may be molded, for example, via injection molding. Exemplary suitable materials from which the rig base 220 may be made include polystyrene (PS), high impact polystyrene (HIPS), SAN, ABS, PC, ABS/PC blend, and other resin materials. The material can be chosen as desired based on various factors, such as, for example, strength, rigidity, surface hardness, and/or chemical inertness. Suitable manufacturing techniques include, but are not limited to, for example, injection molding, reaction injection molding, casting, and machining.

Figure 10A:
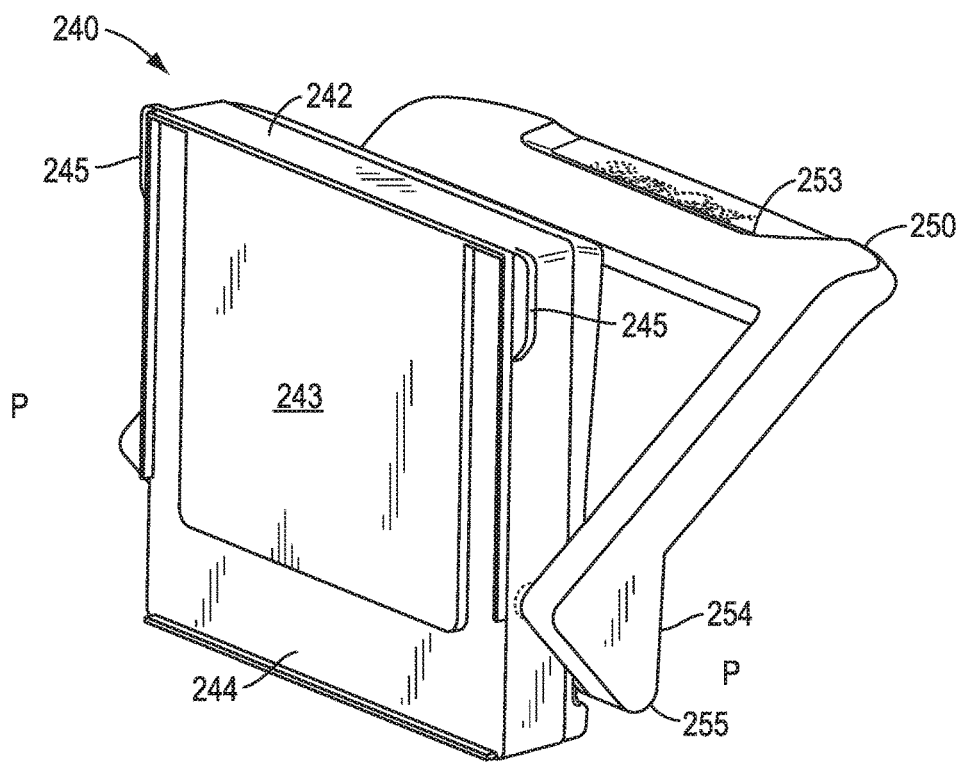
FIGS. 10A-10C are various views of an exemplary embodiment of a clamping mechanism of the casting rig of FIG. 7 in an open configuration.
Figure 10B:
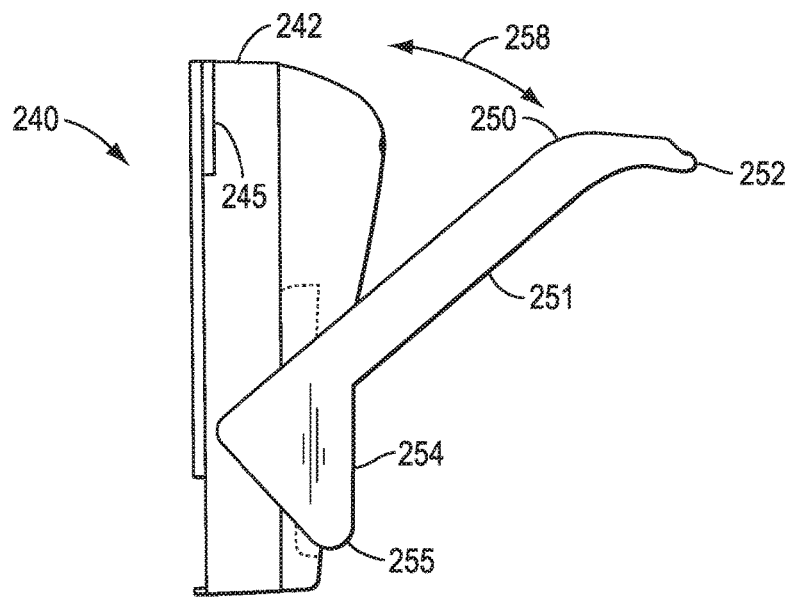
Figure 10C:
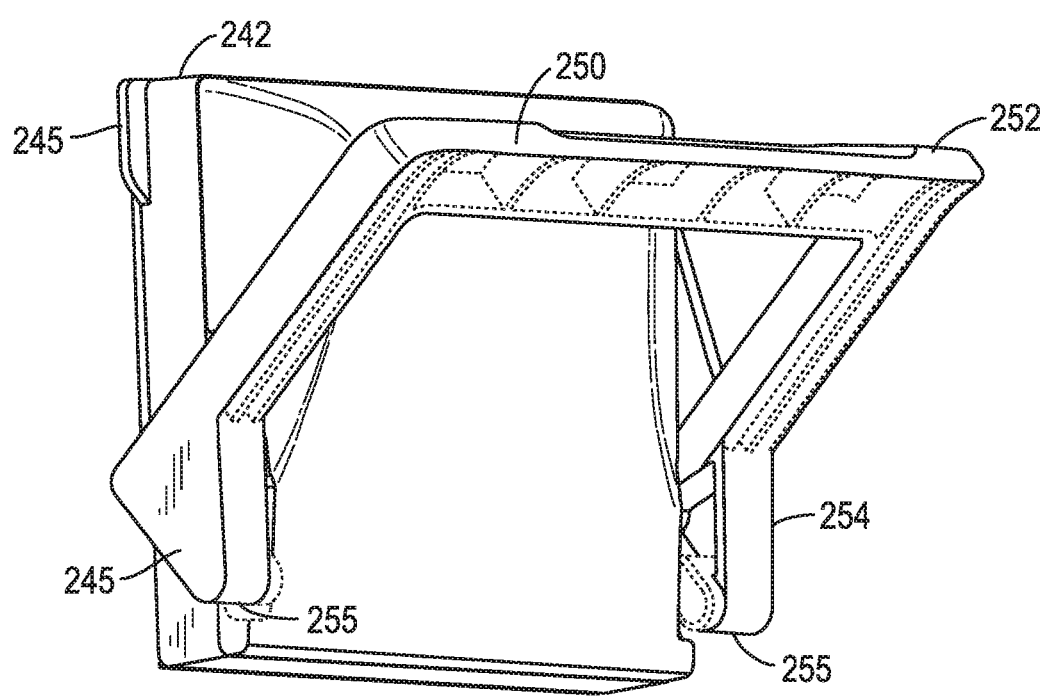

Referring now to the exemplary embodiments of FIGS. 9 and 10, the clamping mechanism 240 of the casting rig 200 is depicted. FIGS. 9 and 10 show the clamping mechanism 240 in isolation removed from the rig 200. FIGS. 9A-9C show the clamping mechanism 240 in a closed configuration in which, if positioned in the rig 200, the clamping mechanism 240 would be in a position to clamp a cassette in the rig 200. The views of FIGS. 9A-9C are front perspective, side, and rear perspective, respectively. FIGS. 10A-10C show the clamping mechanism 240 in an open configuration in which, if positioned in the rig 200, the clamping mechanism 240 would be in a position to permit insertion or removal of a cassette into the rig 200. As with FIGS. 9A-9C, the views of FIGS. 10A-10C are front perspective, side, and rear perspective, respectively.

As illustrated in FIGS. 9 and 10, the clamping mechanism 240 comprises a clamping plate 242 and a handle 250 that is rotatably coupled to the clamping plate 242, for example, via a pivot pin/recess coupling 246. The clamping plate 242 has a generally planar front face area 243 sized and shaped to generally correspond to at least the size and shape of the area of the cassette 100 between the boundaries of the lower edge of the cut out region 115 and the inner edges of the right and left sides of the spacer mechanism 130 and the upper edge of the slot opening 122. Surrounding this front face area 243 is a recessed area 244 that extends around the side and bottom edges of the front face of the clamping plate 242. In the exemplary embodiment depicted, the recessed area 244 is thus generally U-shaped. As described further below, the recessed area 244 is configured to receive the sealing pad 260. The overall outer dimensions of the clamping plate 242 are selected to interact with the inner surface stepped profile of the upright portions 223 of the rig base 220, as will be described in further detail below. At least the front face portion 243 of the clamping plate 242 can have a color that assists in facilitating observation of the gel being poured and formed in the gel cassette as it is held in the casting rig.

The handle 250 of the clamping mechanism 240 has two side legs 251 and a grasping region 252 connecting the two side legs 251. Thus, as depicted, the handle 250 can have a generally inverted U-shape in the orientation of the clamping mechanism 240 positioned in the rig base 220 during use for casting an electrophoresis gel. The grasping region 252 may be provided with a surface profile or features that provide comfort and facilitate grasping and rotation of the handle 250 by a user. For example, in the exemplary embodiment depicted in FIGS. 9 and 10, the handle 250 can include a recessed area 253 and be slightly flared outwardly to provide a comfortable and accessible grasping configuration for a user.

The handle 250 is rotatably coupled to the clamping plate 240 toward ends of the side legs 251. In an exemplary embodiment, pins (not shown) may extend radially inwardly from each of the legs 251 and be received in apertures (also not shown) in the sides of the clamping plate 242. In this way, the handle 250 can pivot around the pins for rotational movement of the handle 250 relative to the clamping plate 240 in directions of the double-headed arrows 258 to move the handle 250 between the closed and open positions shown respectively, for example, in FIGS. 9B and 10B. Those having ordinary skill in the art would appreciate that the pins and recesses on the handle 250 and clamping plate 240 could be reversed, and that other coupling mechanisms can be used to rotatably mount handle 250 relative to clamping plate 240, without departing from the scope of the present disclosure or claims.

As mentioned above and as will be appreciated from the explanation further below, an embodiment in accordance with the present disclosure uses a clamping mechanism with a cam feature that interacts with the rig base to provide a clamping force sufficient to hold a gel cassette stably in place in the casting rig, while also serving to lock the clamping mechanism and cassette stably in position in the rig. With reference to FIGS. 9 and 10, camming protrusions 254 are provided at the ends of the side legs 251 of the handle 250. The camming protrusions 254 extend generally perpendicularly and rearwardly from the side legs 251 of the handle 250 (i.e., in a direction away the front face portion 243 of the clamping plate 240. As best shown in FIG. 9B, in the closed configuration of the handle 250, the camming protrusions 254 jut out past the rear face of the clamping plate 240 and past the handle 250. As best shown in FIG. 10B, in the open configuration of the handle 250, the camming protrusions 254 move so as to present an approximately flush surface profile with a rear face of the clamping plate 240. In this position, the grasping region 252 of the handle 250 extends rearwardly further than the camming protrusions 254. In one exemplary embodiment, in the closed configuration of the handle 250, as depicted in FIGS. 9A-9C, the center of the radius of curvature of the camming surface 255 of the camming protrusion 254 is above (in the orientation of the drawings) the pivot axis P of the handle 250, although such an arrangement is nonlimiting and exemplary only. In such a configuration, as described further below, the handle and camming surface 255 (in cooperating with the rear wall of the rig base), provide an over-center locking configuration to help ensure the handle 250 remains in the closed configuration when clamping a cassette unless a sufficient force is exerted on the handle to move and overcome the frictional engagement between the camming surfaces and the rear wall of the rig base.

In the exemplary embodiment depicted, the camming protrusions 254 have a generally triangular shape with a base connected to the handle side legs 251 and terminating in a rounded tip that provides the camming surface 255, with the rounded tip moving between a position in which it juts out rearwardly relatively to the clamping plate 240 (i.e., in the closed configuration of the handle 250) and a position in which it points generally downwardly (i.e., in the open configuration of the handle 250). Providing the rounded tip camming surface 255 can assist in reducing friction during engagement with the base, as will be discussed further below. Although camming protrusions 254 have a generally triangular shape, those having ordinary skill in the art would appreciate that other shapes, such as semi-circular, oblong, etc. also may be employed without departing from the scope of the present disclosure and claims.

As with the rig base 220, the clamping plate 240 and the handle 250 may be made of a variety of materials. In an exemplary embodiment, the clamping plate 240 and handle 250 may be made of plastic and may be injection molded. Such materials and manufacturing techniques can facilitate cleaning and promote efficiency in production of the parts. Exemplary suitable materials from which the clamping plate 240 may be made include PS, HIPS, SAN, ABS, PC, ABS/PC, and other resin materials. The material can be chosen as desired based on various factors, such as, for example, strength, rigidity, surface hardness, and/or chemical inertness. Exemplary suitable materials from which the handle 250 may be made include, for example, polyoxymethylenes (POM), such as, for example, Delrin or acetal, or nylons, for combinations thereof. The material for the handle can be chosen as desired based on various factors, such as, for example, strength, rigidity, surface hardness, chemical inertness, and/or sufficiently low friction between the handle and the clamping plate and rig base to permit relatively smooth motion. Suitable manufacturing techniques for the clamping plate and the handle include, but are not limited to, for example, injection molding, reaction injection molding, casting, and machining.

Figure 11:
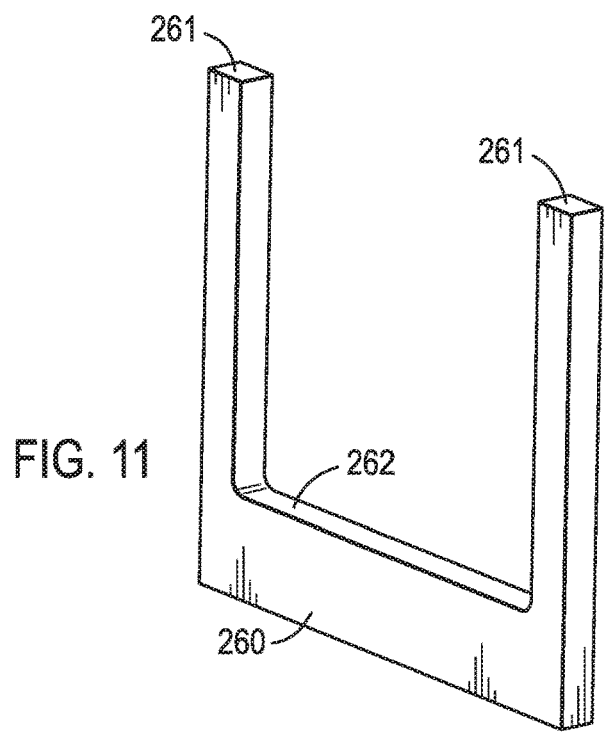
FIG. 11 is a perspective view of an exemplary embodiment of a sealing pad of the casting rig of FIG. 7 in accordance with the present disclosure.
Figure 12:
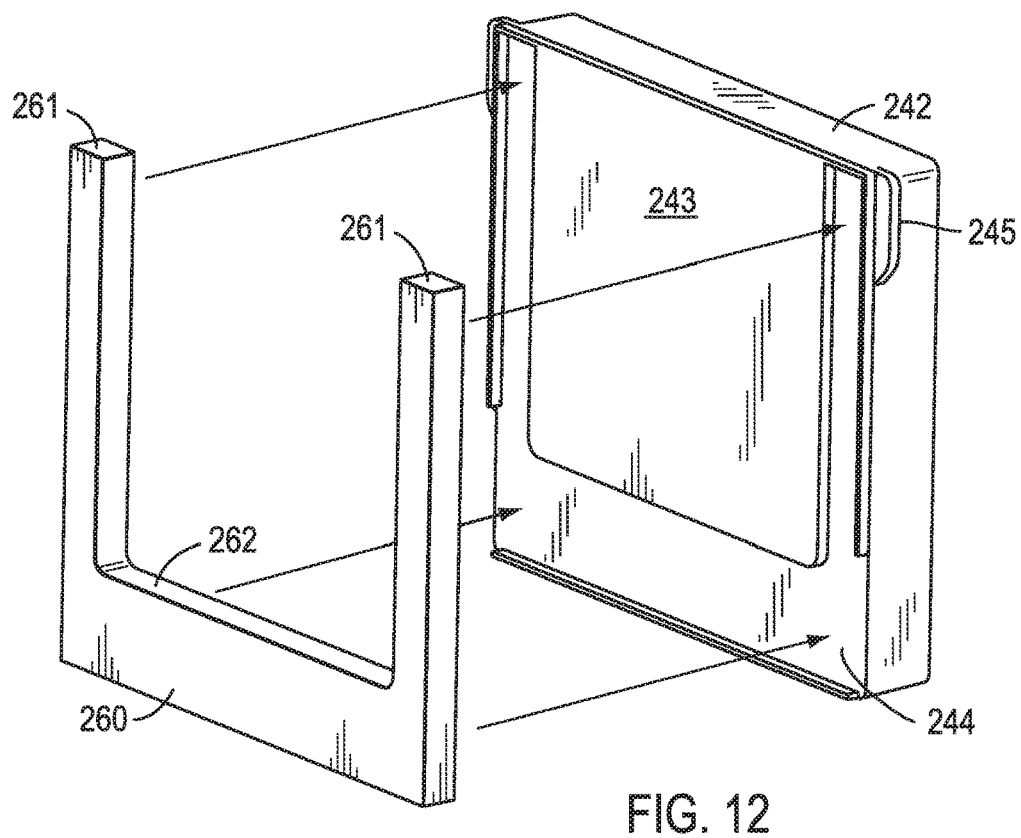
FIG. 12 is a view showing the alignment of the sealing pad of FIG. 11 with a clamping plate of the clamping mechanism of FIGS. 9-10 in accordance with the present disclosure.

In addition to the rig base 200 and the movable clamping mechanism 240, the casting rig 200 further comprises an elastically compressible sealing pad 260 that is configured to be positioned between the front of the clamping plate 242 and a cassette 100 when using the rig 200 to prepare electrophoresis slab gel. FIG. 11 depicts the sealing pad 260 in isolation, and FIG. 12 shows the sealing pad 260 in alignment with the clamping plate 240 prior to being placed in contact with the clamping plate 240. As discussed above, the clamping plate 242 has a recessed area 244 that surrounds the planar front face are 243 and is configured to receive the sealing pad 260. Accordingly, the dimensions of the sealing pad 260 are configured to fit within the recessed area 243, again defining a generally U-shape so as to leave an open region to expose and provide visibility to the majority of the cassette 100. In an exemplary embodiment, the sealing pad 260 can have side legs 261 that approximately correspond to the dimensions of the side legs of the spacer 130 of the cassette 100. However, the lateral leg 262 of the sealing pad 260 that connects the side legs 261 will have a width (measured in a direction parallel to the legs 261) that is larger than the corresponding part of the spacer so that when the clamping mechanism 240 with the sealing pad 260 clamps the cassette in position in the rig base 220, the sealing pad 260 covers and seals against the slot opening 122 in the cassette.

In an exemplary embodiment, the sealing pad 260 is made of an elastically compressible material that is sized to provide a cushion against a cassette during clamping of the cassette in the rig 200. In addition to providing a cushion, the sealing pad 260 is compressible so as to provide a sufficient clamping force to both stably hold the cassette in position in the casting rig 200 and, in various exemplary embodiments, also to seal the plates 110, 120 against the spacer mechanism 130. In various exemplary embodiments, the thickness of the sealing pad 260 when uncompressed may range from about 1 mm to about 20 mm, for example, the thickness may be about 6.35 mm when uncompressed. The sealing pad 260 may further be configured to compress to about 10% to about 50% of its original thickness, for example from about 20% to about 40%. In an exemplary embodiment, when the sealing pad has a thickness of about 6.35 mm when uncompressed, the thickness may range from about 3.75 mm to about 5 mm when the sealing pad is compressed.

Various materials may be employed for the elastically compressible sealing pad 260. It is desirable that the sealing pad 260 be made of a material that permits it to spring back substantially to its original thickness and shape after compression, so as to permit the sealing pad 260 to be used a number of times prior to having to be replaced. Moreover, the material used for the sealing pad may desirably have relative low friction and be configured to be subject to repeated use without significant wear and breakdown of the material. In various exemplary embodiments, the sealing pad 260 can be made of a type of foam, such as for example, a low compression set, closed-cell foam. Exemplary non-limiting foam materials that can be used for the sealing pad 260 include silicone, ethylene propylene diene monomer rubber (EPDM), polyurethane, and polyethylene, and combinations thereof.

The sealing pad 260 can be separate from the clamping plate 240 and received in an unattached condition in the recessed area 243 in use of the casting rig. In an alternative exemplary embodiment, the sealing pad 260 can be affixed to the recessed area 243 of the clamping plate 240, such as for example, via an adhesive. For example, the sealing pad 260 may include an adhesive backing on one side, with a protective peel-away strip (not shown) that maintains the adhesive from drying out and permits exposure of the adhesive when it is desired to affix the sealing pad 260 to the recessed area 243 of the clamping plate 240. In this way, the sealing pad 260 can be relatively easily replaced when needed by removing the sealing pad 260 from the clamping plate 240 and replacing it with another adhesive-backed sealing pad 260. In various other exemplary embodiments, adhesive such as, for example, glue, epoxy, or a high-tack adhesive may be used to affix the a sealing pad, for example, as a permanent portion of the clamping plate.

In exemplary embodiments wherein the sealing pad 260 is made of a foam material, compression of the sealing pad 260 can result in gases escaping from the foam material. Because the sealing pad 260 is placed over to seal the slot opening 122 in the cassette 100, gas escaping from the sealing pad 260 can potentially be introduced through the slot opening 122 and negatively impact formation (e.g., polymerization) of the gel in the cassette 100. Thus, in various exemplary embodiments, it is desirable to provide a barrier layer between any potential gas leakage from the sealing pad 260 and the slot opening 122. Such a barrier layer may be a non-porous film, such as, for example, made of plastic, such as, for example, polypropylene, polyethylene, Kapton, Teflon, or the like, positioned over the slot opening 122 so as to be arranged between the sealing pad 260 and the cassette 100 when the cassette 100 is clamped in the casting rig 200. The barrier layer can be provided on a surface of the sealing pad 260 opposite to the adhesive backing and facing away from the clamping plate 240 in a position of the sealing pad 260 in use for clamping the cassette 100 in the rig during pouring of the gel. For example, the barrier layer may be provided over the entire surface of the legs 261 and lateral connecting portion 262, or at least on a portion of the lateral connecting portion 262 that covers the slot opening 122. In another exemplary embodiment, the barrier layer may be provided as a small film, such as tape, adhered over the slot opening 122 on the back surface of the back plate 120 of the cassette 100.

Although the exemplary embodiment of the rig described above is an assembly of multiple separate parts configured to be put together in a cooperating manner, those having ordinary skill in the art would appreciate that the assembly, in particular the clamping mechanism and rig base, could be integrally coupled together and/or molded as a single piece construction. Providing the parts as separate, can facilitate access to various surfaces for cleaning and also may make replacement of parts more efficient.

Figure 13A:
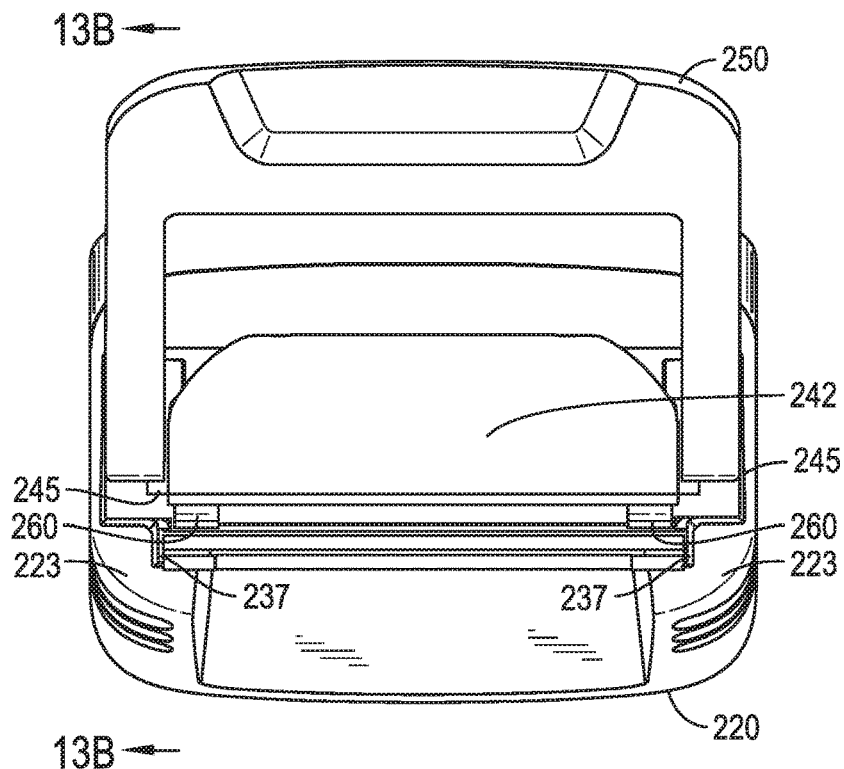
FIG. 13A is a top view of the casting rig of FIG. 7 loaded with the cassette of FIG. 4 with the casting rig in an open configuration.
Figure 13B:
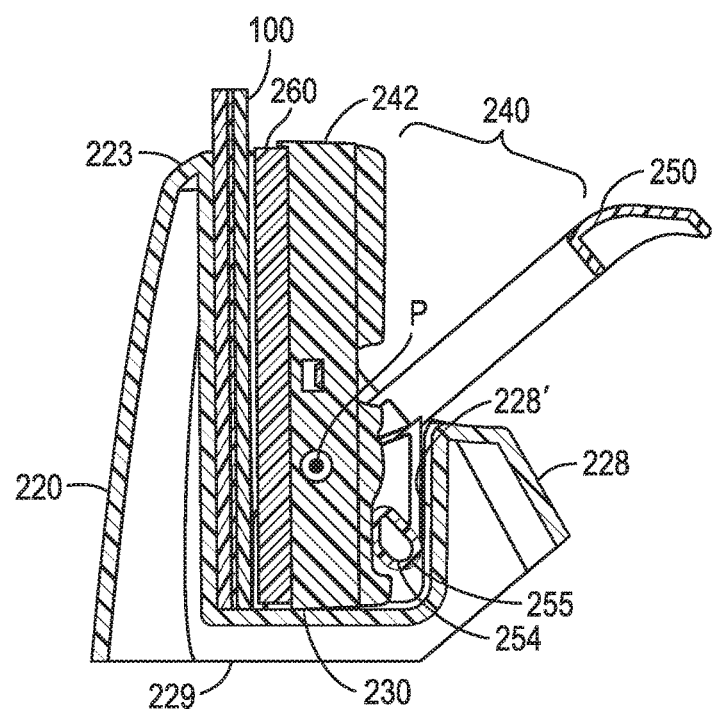
FIG. 13B is a cross-sectional view of FIG. 13A taken through line 13B-13B.
Figure 14A:
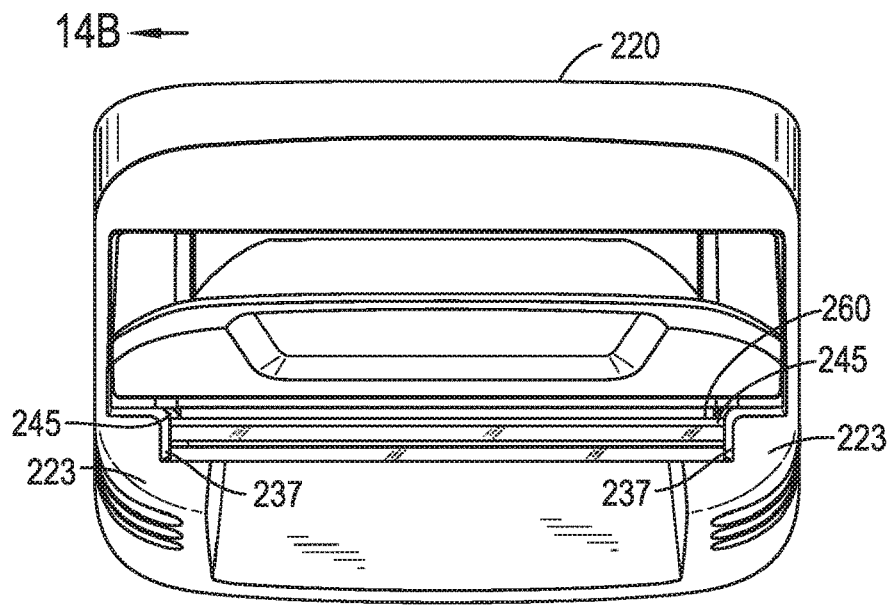
FIG. 14A is a top view of the casting rig of FIG. 7 loaded with the cassette of FIG. 4 with the casting rig in a closed configuration.
Figure 14B:
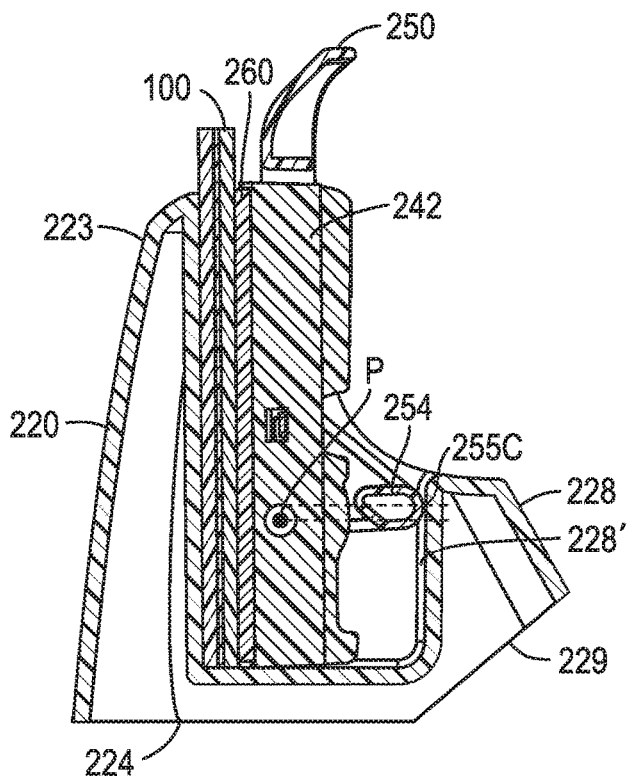
FIG. 14B is a cross-sectional view of FIG. 14A taken through line 14B-14B.
Figure 15:
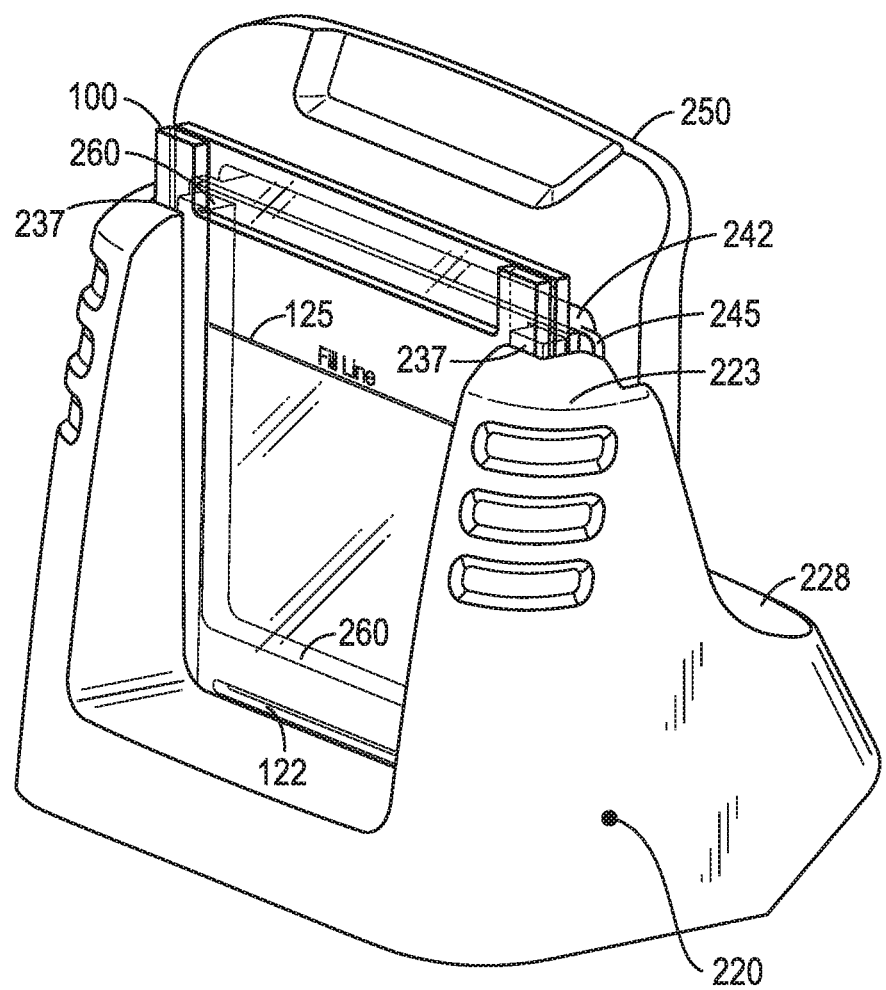
FIG. 15 is a front perspective view of the casting rig of FIG. 7 loaded with the cassette of FIG. 4 with the casting rig in a closed configuration.

Turning now to FIGS. 13-15, the casting rig 200 is shown as an assembly receiving the cassette 100 in an open configuration (FIGS. 13A and 13B) and a closed, clamping configuration (FIGS. 14A, 14B, and 15). FIGS. 13A and 14A are top views, FIGS. 13B and 14B are longitudinal cross-section side views, and FIG. 15 is a front perspective view of the casting rig 200 and cassette 100. As can be seen in FIGS. 13A and 13B, in the open configuration of the casting rig 200, the clamping mechanism 240 is received in the opening of the rig base 220, resting on the bottom support surface 230. In the open configuration, the handle 250 tends to pivot away and at an angle from the clamping plate 242, positioning the camming protrusion 254 so that the camming surface generally points downwardly rather than rearwardly, as described above. In this position, the front face of the clamping plate 242 with the sealing pad 260 positioned in the recessed area 244 is spaced from the inside surface of the uprights 223 of the rig base 220 sufficiently to permit the gel cassette 100 to be inserted as illustrated. As discussed above, the interior surfaces of the upright portions 223 have a stepped profile extending generally vertically from the top, free ends of the upright portions 223 to the bottom support surface 230 of the rig base 220. As best shown in FIGS. 13A and 14A, the stepped profile provides a laterally inwardly positioned surface portion 237 that provides an enclosure wall sized to receive the cassette 100 in a snug fashion so as to substantially prevent lateral movement of the cassette 100.

To clamp the cassette 100 within the rig for casting of the slab gel, the handle 250 can be rotated about the pivot axis P and rotatable pin coupling 246 from the position in FIGS. 13A and 13B to the position shown in FIGS. 14A-15, corresponding to the closed configuration of the rig 200. As the handle 250 is rotated to its limit shown in FIGS. 14-15, the camming surface 255 of the camming protrusion 254 rides against the inner surface 228' of the rear wall 228. The interaction of the camming protrusion 254 and the inner surface 228' of the rear wall 228 assists in moving the clamping plate 240 toward the uprights 223 of the rig base 220 once the initial motion is started, while also providing an effective clamping force due to the force of the inner surface 228' acting on the camming protrusion 254, and thus pushing the clamping plate 240 toward the uprights 223. The clamping mechanism 240 thus provides a single rotational motion by which to clamp the cassette 100 in the rig 200. With the cassette 100 in the position illustrated in FIGS. 13-15, the tolerances of the cassette 100, casting rig 200, and sealing pad 260 cause the cassette 100 to be clamped between the uprights 223 and the sealing pad 260. As can be seen in FIGS. 14A and 14B, the clamping force causes the sealing pad 260 to compress in thickness, and the plates 110, 120 of the cassette 100 to be sealed against the spacer mechanism 130.

As seen best in the top views of FIGS. 13A and 14A, laterally outwardly extending tabs 245 may be provided on the clamping plate 242. These tabs 245 can present a stop against the handle 250 to prevent it from continuing to move forward past the tabs 245.

As shown in FIG. 14B, the contact location 255C where the camming surface 255 meets the inner surface 228' of the rear wall 228 can be aligned with or offset from the pivot axis P of the handle 250 and camming protrusion 254. For example, as depicted in FIG. 14B, the contact location 255C lies above the pivot axis P. In this way, the camming protrusion 254 can be self-locking, tending to push the handle 250 toward the closed configuration once it has been rotated to a certain degree. Moreover, the arrangement requires a greater force to move the handle 250 from the closed configuration of FIGS. 14A and 14B to the open position of FIGS. 13A and 13B than would be required if the contact point 255C were aligned with or below the pivot axis P in the position of the handle 250 of FIGS. 14A and 14B.

In the closed configuration of the casting rig 200, as depicted in FIGS. 14 and 15 for example, the cassette 100 is clamped by the clamping plate 240 and sealing pad 260 under a force sufficient to seal the plates 110, 120 against the spacer mechanism 130, and to seal the sealing pad 160 against the slot opening 122 in the back plate 120. With those seals established, the liquid solution (e.g., a polyacrylamide solution) for forming the electrophoresis slab gel can be introduced into the cassette 100, for example, via a pipette (e.g., serological pipette) or other loading mechanism moving along the cutout portion 115 between the plates 110, 120. Because the casting rig 200 firmly supports and holds the cassette 100, a user's hands can remain free to fill the cassette 100 without having to also stabilize the cassette 100.

Figure 16:
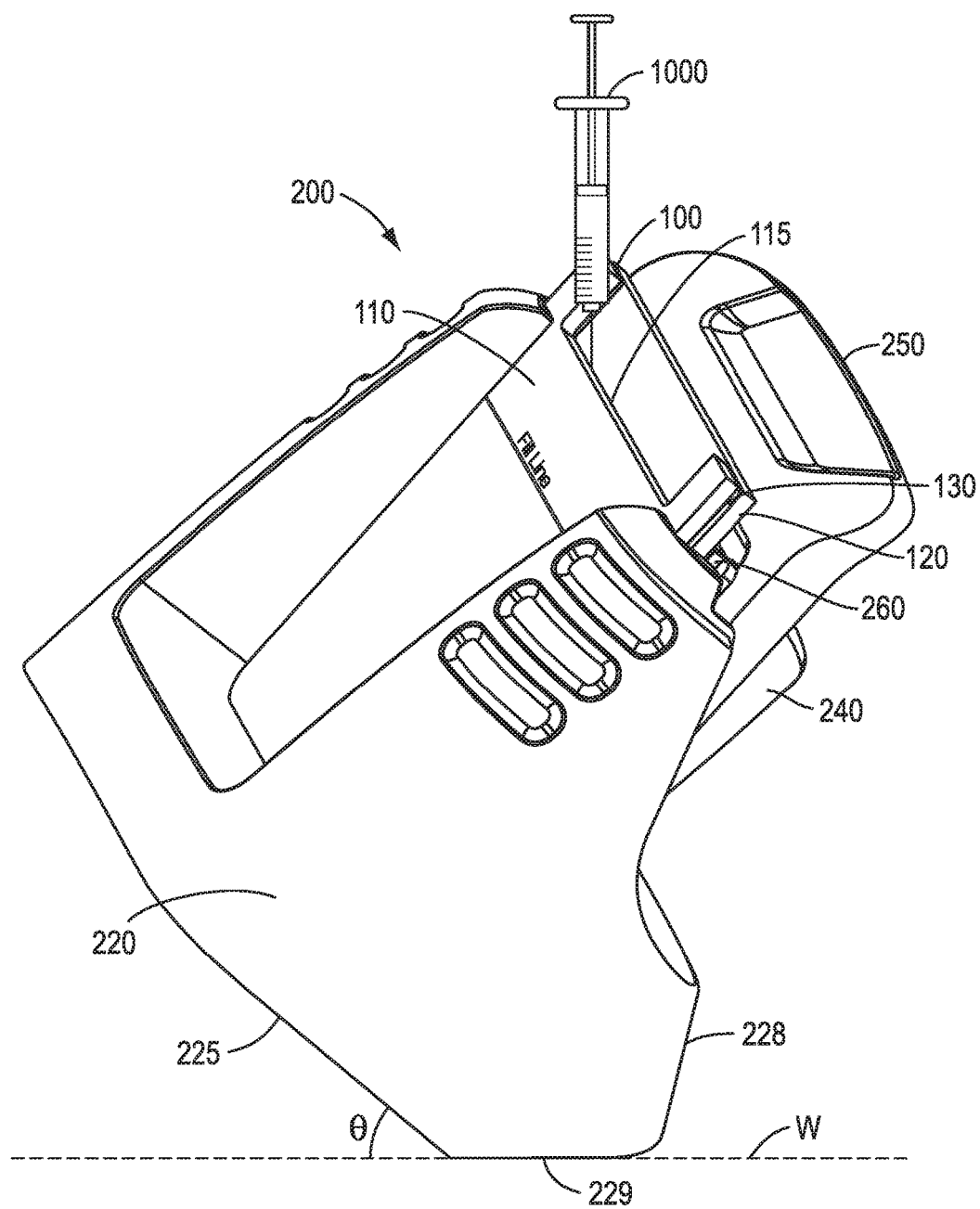
FIG. 16 is a front perspective view of the casting rig of FIG. 7 loaded with the cassette of FIG. 4 with the casting rig in a closed and tilted configuration for loading sample into the cassette in accordance with an exemplary embodiment of the present disclosure.

In an exemplary embodiment, as shown in FIG. 16, to further facilitate loading of the cassette 100 with the solution for forming the gel, the casting rig 200 and the clamped cassette 100 can be tilted so as to rest on the angled surface 229 of the rig 200 on a work surface W. The surface 229 is sufficient to allow the rig 200 loaded with the cassette 100 to repose stably in a tilted position, again allowing a user's hands to remain free to fill the cassette 100. In addition, tilting the casting rig 200 can provide a desired orientation of and access to the cutout region 115, with the space between the front and back plates 110,120 being presented as a V to facilitate loading of the cassette 100, for example via a pipette 1000 depicted in FIG. 16. In various exemplary embodiments, the configuration of the surface 229 and rig 200 can be such as to allow the rig to rest in at a tilt angle Θ ranging from about 30 degrees to about 70 degrees, for example about 40 degrees, about 45 degrees, or about 50 degrees. Once the solutions for the gel have been loaded into the cassette 100, the rig 200 can be tilted back to the position shown in FIG. 15, with the surface 225 resting on the work surface and the cassette 100 in a substantially upright position relative to the work surface. The gel can be allowed to polymerize in this upright position of the rig 200 and clamped cassette 100.

Once the gel has been polymerized in the cassette 100, and optionally wells formed in the gel with a comb as described above with reference to FIGS. 3A and 3B for example, the cassette 100 can be removed and moved to a buffer tank to perform electrophoresis, as those of ordinary skill in the art are familiar with. To assist a user in providing a visual boundary for loading sample in well-defined and uniformly spaced lanes in the otherwise transparent gel, an accessory loading guide tool can be positioned relative to the cassette proximate to where sample is loaded to assist in proper alignment during sample loading.

The present disclosure contemplates an accessory tool that combines a loading guide with a gel trimming wedge feature. Such a combination can provide efficiencies in the overall loading of sample into the formed slab gel for electrophoresis, and also for removing and trimming the gel for post-electrophoresis analysis. Although various exemplary embodiments described below illustrate an exemplary embodiment of such an accessory tool being used with the gel cassette 100, the accessory tool is not limited to use with such a gel cassette configuration, but can be used and modified if needed to be used with a variety of gel cassette configurations and formats.

Figure 17:
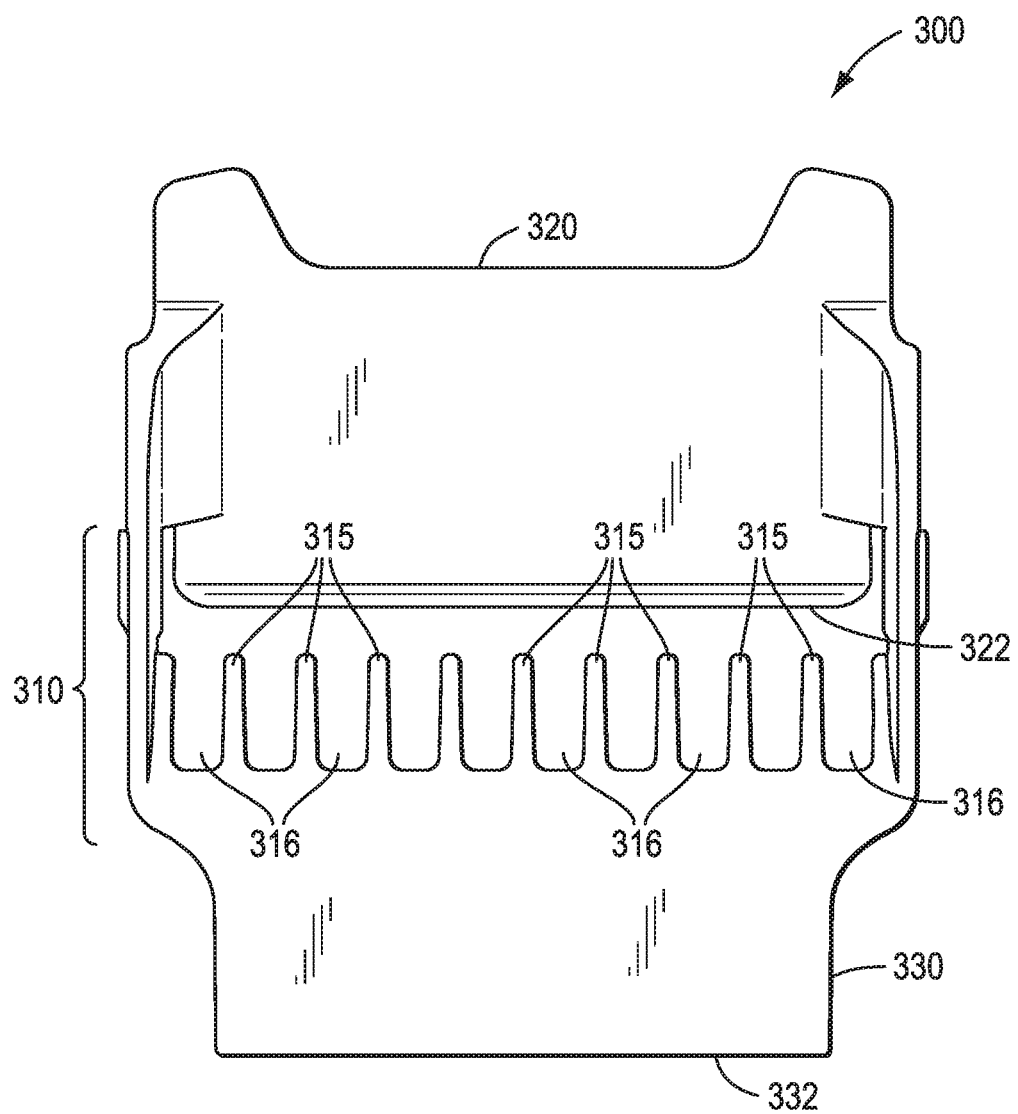
FIG. 17 is a front view of an exemplary embodiment of an accessory loading guide tool in accordance with the present disclosure.
Figure 18A:
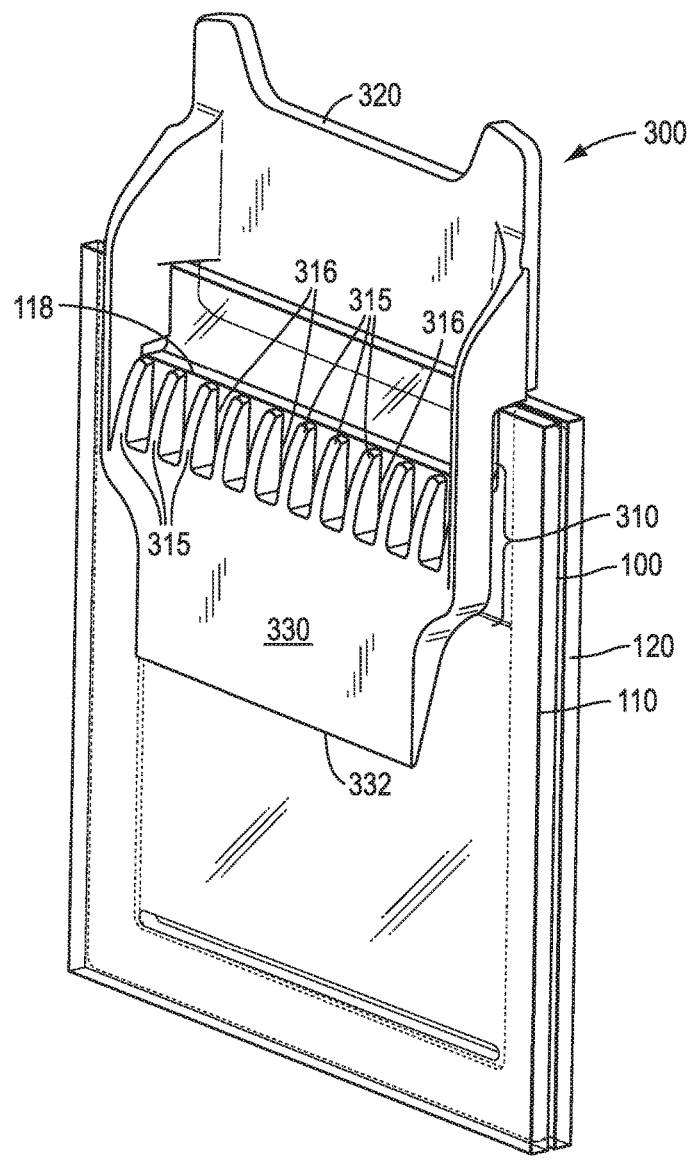
FIGS. 18A and 18B are front perspective and side views of the accessory loading guide tool of FIG. 17 positioned for use on the cassette of FIG. 4 in accordance with the present disclosure.
Figure 18B:
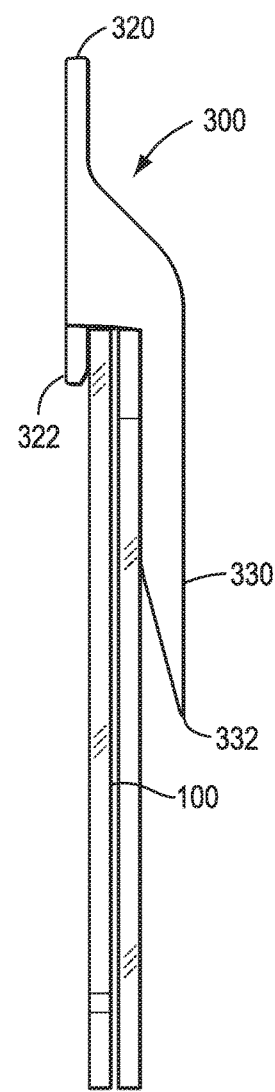

Referring now to FIGS. 17-18, an exemplary embodiment of an accessory loading guide tool in accordance with present disclosure is depicted. FIG. 17 is a front perspective view of the loading guide tool 300 in isolation. FIGS. 18A and 18B, are front perspective and side views showing the tool 300 positioned for use on a cassette, such as cassette 100. As shown, the tool 300 has a comb portion 310 that includes a plurality of teeth 315. The teeth 315 are spaced from each other so as to form a plurality of valleys 316 between adjacent teeth 315. In this way, and as can be seen with reference to FIG. 18A, when the tool 300 is placed in position on a gel cassette 100, the valleys 316 surrounded by teeth 315 serve as a mechanism to define virtual wells to aid in the loading of the gel cassette 100 to perform electrophoresis.

The tool 300 includes a handle portion 320 that extends upwardly from lateral ends of the comb portion 310 and also is positioned slightly rearwardly (in the orientation of FIGS. 17-18) from the ends of the comb portion 310. The connection between the handle portion 320 and the comb portion 310 provides a surface configured to receive a top edge of the cassette such that the tool 300 rests like a hook over the cassette. In this way, the teeth 315 of the comb portion 310 are positioned in alignment across the portion of the cassette in which sample is to be loaded to define the lanes for electrophoresis analysis. In other words, the tool 300 is configured such that the cassette (see cassette 100 in FIGS. 18A and 18B) is positioned in the space between the comb portion 310 and the handle portion 320, with the comb portion 310 resting on the front plate 110 of the cassette 100 and the lower end 322 of the handle portion 320 resting on the back plate 120 of the cassette 100. For example, the top free ends of the comb teeth 315 can be approximately aligned with the lower edge of the cutout region 115 of the front plate 110, as best seen in FIG. 18A. Accordingly, when loading sample into the gel cassette 100 for electrophoresis, a pipette or other loading device can be positioned in the cutout region 115 in alignment with each valley 316 between adjacent teeth 315 to load sample in well-defined lanes between the front and back plates 110, 120.

Although the exemplary embodiment of FIGS. 17-18 show a comb portion 310 having 10 valleys 316, the number and configuration of the valleys 316 between adjacent teeth 315 is non-limiting and exemplary only, and more or less valleys and teeth can be provided, such as, for example, from 1-20 valleys, for example, 12, 15, or 17 valleys. In various exemplary embodiments, the overall width of the comb portion 310 may remain the same, with the width of the valleys 316 (and thus lanes defined) changing depending on the number of valleys 316 provided. However, those of ordinary skill in the art would appreciate that overall dimensions of the loading guide tool 300 also may vary to correspond to various formats and sizes of gel cassettes and electrophoresis systems.

Figure 19:
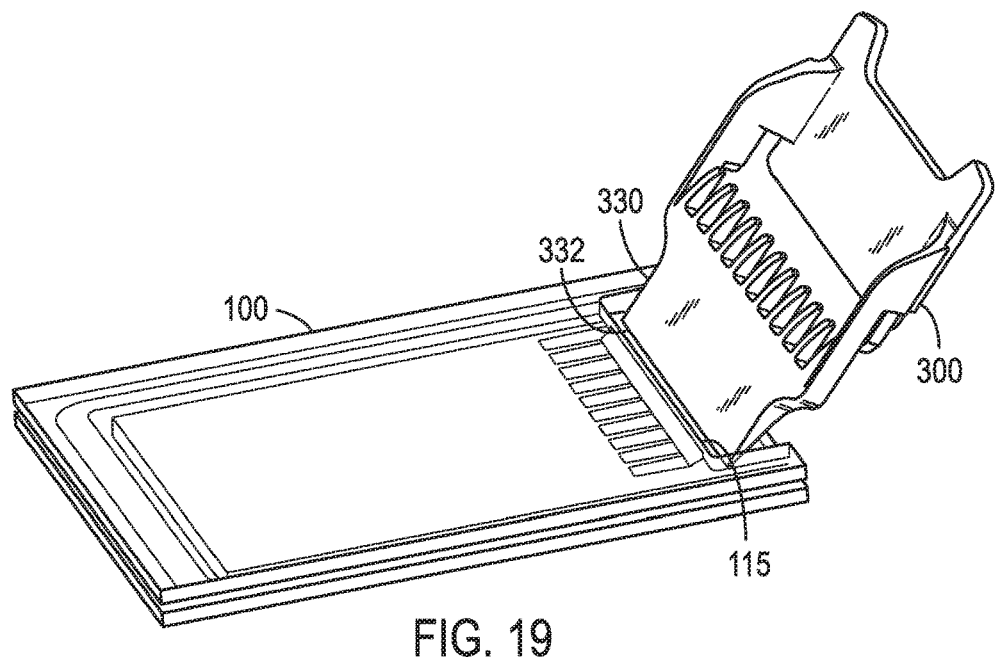
FIG. 19 is a perspective view showing use of the accessory loading guide tool of FIG. 17 for opening a cassette in accordance with the present disclosure.

The loading guide tool 300 further includes a wedge portion 330 that extends from the comb portion 310 in an opposite direction from handle 320 and from the free ends of the teeth 315. The wedge portion 330 is generally tapered in a direction from the comb portion 310 to a free edge 332 that terminates in a relatively sharped-edged profile. With this configuration, in addition to being used as a comb to define virtual lane guides to introduce sample, the wedge portion 330 of the accessory tool 300 also can be used to assist in opening a cassette to recover the gel and/or as a blade to trim the slab gel recovered from the gel cassette after electrophoresis. For example, with reference to FIG. 19, after electrophoresis is completed, the cassette 100 can be removed from the buffer tank, and the edge 332 of the wedge portion 330 can be inserted between the front and back plates 110, 120, such as for example in the cutout region 115 of cassette 100 shown in FIG. 19, and used to separate the plate 110 from the plate 120 and the slab gel. Although FIG. 19 illustrates the edge 332 of the wedge portion 330 being inserted between the plates in the cutout region 115, those having ordinary skill in the art would appreciate that the wedge portion 330 may be placed between and used to separate the plates 110, 120 to recover the slab gel at other locations along the edges of the cassette 100.

Figure 20:
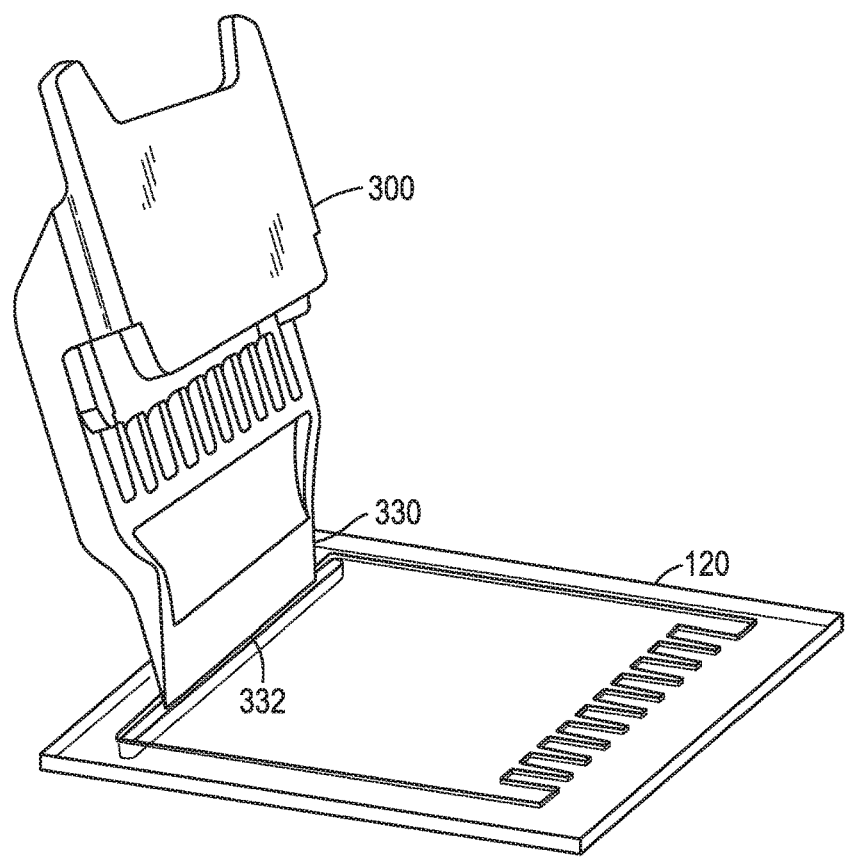
FIG. 20 is a perspective view showing use of the accessory loading guide tool of FIG. 17 for trimming a recovered electrophoresis gel in accordance with the present disclosure.

After the plates 110, 120 of the cassette 100 have been separated, whether using the wedge portion 330 or otherwise, the sharp-edged profile 332 of the wedge portion 330 can be used as a blade to trim the recovered slab gel, which may be useful for post-electrophoresis analysis. In an exemplary embodiment shown in FIG. 20, when a gel cassette having the configuration of cassette 100 is used, the sharp-edged profile 332 of the wedge portion 330 can be used to trim excess portions of the slab gel 500 extending beyond the upper edge of the slot opening 122. In addition, a portion of the formed gel may be thickened in a region corresponding to where the gel fills the slot opening 122, and the sharp-edged profile 332 of the wedge portion 330 also can be used as a blade to trim this extra thickness from the gel, sometimes referred to as the "foot" of the gel. However, those having ordinary skill in the art would appreciate that any portions of the slab gel may be trimmed as desired.

A variety of materials may be used to make a loading guide tool in accordance with exemplary embodiments of the present disclosure. Various exemplary embodiments contemplate making the loading guide tool out of plastic, for example, via molding, such as injection molding in a single, monolithic piece construction. It is desirable to make the loading guide tool out of a material that is relatively durable, including to permit the wedge portion to be used as a gel trimming tool, and/or easy to clean, so as to permit reuse of the tool. Exemplary suitable materials that may be used to make the accessory loading guide tool include, but are not limited to, PS, HIPS, ABS, ABS/PC, PC, and other similar materials.

In accordance with various exemplary embodiments, the present disclosure contemplates a kit for the preparation of an electrophoresis slab gel that may include one or more of the following: a casting rig base and clamping mechanism; one or more replaceable sealing pads; a gel cassette, which may include one or more of front and back plates and one or more replaceable spacer mechanisms in accordance with various exemplary embodiments; solutions for forming the polymerized gel, including stacking and/or resolving gels; one or more loading guide tools and one or more well-forming comb tools, each of which may come in different well number formats, for example. Those having ordinary skill in the art would appreciate that kits contemplated by the present disclosure may be sold in various combinations of components and number of items in a kit as desired.

In accordance with an exemplary embodiment, a method for preparing and using an electrophoresis slab gel in accordance with the present disclosure may include, after preparation of the solutions for forming the gel, setting the casting rig (e.g., base 200 with clamping mechanism 240 and sealing pad 260 inserted in base 200) on a level work surface, aligning and assembling the front and back plates of a cassette together with the spacer mechanism sandwiched and aligned in between (e.g., plates 110, 120 and spacer mechanism 130), and positioning the assembled cassette into the casting rig (e.g., between the sealing pad and upright portions 223 of base 220). Holding the cassette steady, for example to prevent shifting of the aligned plates and sealing mechanism, the clamping mechanism can then be moved to a closed configuration to clamp (e.g., by rotating the handle 250 of clamping mechanism 240 is a generally single motion to an upright closed configuration) and stably hold the cassette in place, while also creating a force sufficient to seal the cassette. Once the cassette has been clamped and sealed in position using the clamping mechanism of the casting rig, the gel(s) can be poured.

In an exemplary embodiment using the casting rig 200, the casting rig 200 can be tilted such that the surface 229 of the base 220 rests on the work surface and the gel solutions (such as for forming resolving and/or stacking gels) introduced, for example via a pipette, into the cassette (e.g., at the cutout region 115 of cassette 100). During loading of the gel-forming ingredients, a visual inspection for air bubbles also may be performed. Once the cassette has been filled as desired, the casting rig 200 can be tilted back to its initial position with the surface 225 resting on the work surface and the cassette 100 in a substantially upright vertical orientation. Polymerization of the gel can then be allowed to proceed and when completed, the cassette with the formed gel can be removed from the casting rig, for example by rotating the handle 250 of the clamping mechanism 240 to an open configuration to release the clamping force on the cassette.

Optionally, in an exemplary embodiment, a well-forming comb may be inserted into an upper end of the cassette between the plates and into the gel as it polymerizes to form guiding wells for subsequent sample loading, in a manner those having ordinary skill in the art have familiarity with and as described above with reference to FIGS. 3A and 3B. Alternatively or in addition to forming wells in the gel, an accessory loading guide tool 300 can be positioned on the gel cassette after polymerization of the gel to provide visual boundaries of virtual lanes for assisting with loading sample into lanes of the gels, as described above. Finally, if desired, after performing electrophoresis using the gel cassette, the gel can be recovered from the cassette by, for example, separating the front plate 110 from the gel and back plate 120 of the cassette 100. For example, in one exemplary embodiment, the wedge portion 330 of the accessory loading guide tool 300 may be used to separate the front plate 110 from the back plate 120 and to recover the gel. In addition, if desired, the recovered gel can be trimmed using either a separate trimming tool or the wedge portion 330 of loading guide tool 300.

Further modifications and alternative embodiments will be apparent to those of ordinary skill in the art in view of the disclosure herein. For example, the systems, devices, and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

By way of example, the various sizes of the cassette, rig base, clamping mechanism, combs, and/or loading guide structures can be modified to have a variety of dimensions as desired, including so as to be suitable for use with various existing electrophoresis systems, such as, for example the XCell SureLock™ Mini-Cell Electrophoresis System and the XCell SureLock™ Midi-Cell Electrophoresis System, both available from Thermo Fisher Scientific. Moreover, the present disclosure contemplates use of a casting rig and/or an accessory loading guide tool in accordance with various exemplary embodiments with a variety of cassette formats other than those that comprise separate plates and a spacer mechanism sealed together by virtue of a sufficient clamping force as described above. For example, cassettes that may be used with the rigs and/or loading guide tools of the present disclosure may be pre-sealed, for example, by welding or adhesive, with tape or other removable sealing structure provided over the slot of the cassette ultimately used for electrical contact during electrophoresis.

It is to be understood that the particular examples and embodiments set forth herein are nonlimiting, and modifications to structure, dimensions, materials, and methodologies may be made without departing from the scope of the present disclosure and claims including equivalents.

Other embodiments in accordance with the present disclosure will be apparent to those skilled in the art from consideration of the specification and practice of the invention disclosed herein. It is intended that the specification and examples be considered as exemplary only, and that the claims be entitled to their full breadth of scope, including equivalents.

What is claimed is:

1. An apparatus for forming an electrophoresis slab gel, the apparatus comprising:
   a base having an opening configured to receive a cassette configured to contain an electrophoresis slab gel;
   a clamping mechanism configured to move relative to the base between an open position in which the clamping mechanism permits insertion of the cassette into the base, and a closed position in which the clamping mechanism is configured to clamp the cassette received in the base; and
   a compressible pad operatively coupled to the clamping mechanism in a position to compress against a cassette received in the base in the closed position of the clamping mechanism,
   wherein the base is configured to repose in a first position and a second position tilted relative to the first position, and wherein the cassette comprises:
   a first plate and a second plate, each of the first and second plates having an inner face and an outer face;
      a spacer mechanism separate from each of the first and second plates, the spacer mechanism configured to be positioned between the inner faces of the first plate and the second plate, and along aligned side and bottom edges of the first and second plates;
      wherein, when subjected to a clamping force exerted on the outer faces of the first and second plates, the spacer mechanism is configured to:
      maintain a separation distance between the inner faces of the first and second plates, and
      provide a seal to prevent leakage of an electrophoresis gel solution introduced between the plates.

2. The apparatus of claim 1, wherein the first and second plates have equal widths and heights.

3. The apparatus of claim 1, wherein the first and second plates are transparent.

4. The apparatus of claim 1, wherein the first and second plates are made of glass or plastic.

5. The apparatus of claim 1, wherein the spacer mechanism comprises:
   two side legs, the side legs being configured to be positioned along opposite side edges of the first and second plates, and
   a connecting leg extending between the two side legs, the connecting leg being configured to be positioned along the bottom edges of the first and second plates.

6. The apparatus of claim 1, wherein the spacer mechanism is made of a material having a durometer ranging from about 40 A to 80 A.

7. The apparatus of claim 1, wherein the spacer mechanism is made of an elastomeric material.

8. The apparatus of claim 1, wherein at least one of the first and second plates comprises an opening through a thickness of the at least one first and second plate.

9. The apparatus of claim 1, wherein at least one of the first and second plates comprises indicia positioned to indicate a desired fill level of a gel-forming solution.

10. The apparatus of claim 1, wherein, when subjected to a clamping force exerted on the outer faces of the first and second plates, the inner surfaces of the first and second plates and the spacer mechanism define boundaries of a cavity configured to contain a gel-forming solution.

11. The apparatus of claim 1, wherein the spacer mechanism comprises a textured surface.

12. The apparatus of claim 1, wherein the spacer mechanism comprises a first face and a second face facing in opposite directions, wherein at least one of the first face and the second face comprises a stepped profile.

13. The apparatus of claim 1, wherein a top edge of one of the first and second plates has a cutout region.

14. An apparatus for preparation of an electrophoresis slab gel, the apparatus comprising:
   a base having an opening configured to receive a cassette configured to contain an electrophoresis slab gel;
   a clamping mechanism configured to move relative to the base between an open position in which the clamping mechanism permits insertion of a cassette into the base, and a closed position in which the clamping mechanism is configured to clamp a cassette received in the base; and
   a compressible pad operatively coupled to the clamping mechanism in a position to compress against a cassette received in the base in the closed position of the clamping mechanism, wherein the base is configured to repose in a first position and a second position tilted relative to the first position.

15. The apparatus of claim 14, wherein the clamping mechanism comprises a clamping plate and a handle, wherein the handle is pivotably coupled to the clamping plate.

16. The apparatus of claim 15, wherein the handle is configured to move the clamping mechanism between the open and closed positions in response to pivoting of the handle.

17. The apparatus of claim 15, wherein the handle comprises a camming surface configured to interact with the base to cause the clamping plate to exert a clamping force on a cassette received in the base in the closed position of the clamping mechanism.

18. The apparatus of claim 17, wherein a contact location between the camming surface and the base is offset from a pivot axis of the pivotable coupling of the handle to the base.

19. A kit for preparing an electrophoresis slab gel, the kit comprising:
   a first plate and a second plate, each of the first and second plates having an inner face and an outer face;
   a spacer mechanism separate from each of the first and second plates, the spacer mechanism configured to be positioned between the inner faces of the first plate and the second plate, and along aligned side and bottom edges of the first and second plates;
   a base having an opening configured to receive the first and second plates aligned with the spacer mechanism positioned between the inner faces of the first and the second plates, wherein the base is configured to repose in a first position and a second position tilted relative to the first position;
   a clamping mechanism configured to move relative to the base between an open position in which the clamping mechanism permits insertion of the first and second plates with the spacer mechanism disposed therebetween, and a closed position in which the clamping mechanism is configured to clamp the first and second plates to seal against the spacer mechanism disposed therebetween;

a compressible pad configured to be operatively coupled to the clamping mechanism so as to compress against the plates in the closed position of the clamping mechanism;

a loading guide tool comprising a plurality of spaced apart teeth disposed to form a comb structure and a wedge-shaped member extending from the comb structure in a direction opposite to a direction in which free ends of the plurality of teeth extend, the wedge-shaped member terminating in a gel-trimming edge; and ingredients for forming a polymerizable electrophoresis gel.

* * * * *